(12) United States Patent
Winkel et al.

(10) Patent No.: US 9,132,043 B2
(45) Date of Patent: Sep. 15, 2015

(54) PULL-ACTIVATED TAMPON APPLICATOR

(71) Applicant: Kimberly-Clark Worldwide, Inc., Neenah, WI (US)

(72) Inventors: Paula Cardinahl Winkel, Chilton, WI (US); Adrienne Rae Loyd, Neenah, WI (US); Sarah Jane Marie Freiburger, Hortonville, WI (US); Allan James Krueger, Winneconne, WI (US); Betsy Charlotte Fields, San Francisco, CA (US); Vivian Kate Barad, San Francisco, CA (US); Judy May Lee, San Francisco, CA (US); Rebecca Jeanine Sinclair, Palo Alto, CA (US); Adam Patrick Vollmer, San Francisco, CA (US); Dennis J. Boyle, Palo Alto, CA (US); Lukas Martin Scherrer, San Francisco, CA (US); Garry Roland Woltman, Appleton, WI (US); Jonathan Kyle Arendt, Larsen, WI (US); Marcus David Weiher, Sherwood, WI (US); Pamela Mary Thompson, Greenville, WI (US); Angela Ann Johnston, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/253,345

(22) Filed: Apr. 15, 2014

(65) Prior Publication Data

US 2015/0025438 A1    Jan. 22, 2015

Related U.S. Application Data

(63) Continuation of application No. 12/915,224, filed on Oct. 29, 2010, now Pat. No. 8,734,414.

(60) Provisional application No. 61/265,248, filed on Dec. 17, 2009.

(51) Int. Cl.
*A61F 13/20* (2006.01)
*A61F 13/34* (2006.01)
(Continued)

(52) U.S. Cl.
CPC ............... *A61F 13/266* (2013.01); *A61F 13/26* (2013.01); *A61F 13/55185* (2013.01); *A61F 13/2062* (2013.01); *A61F 13/2068* (2013.01); *A61F 13/34* (2013.01)

(58) Field of Classification Search
CPC . A61F 13/2068; A61F 13/2062; A61F 13/26; A61F 13/34
USPC ............................ 604/385.17, 385.18, 11–18
See application file for complete search history.

(56) References Cited

U.S. PATENT DOCUMENTS

| 2,268,536 A | 12/1941 | Seidler |
| 2,355,917 A | 8/1944 | Knight |

(Continued)

FOREIGN PATENT DOCUMENTS

| CH | 224507 | 11/1942 |
| GB | 566869 | 1/1945 |

(Continued)

*Primary Examiner* — Jacqueline Stephens
(74) *Attorney, Agent, or Firm* — Kimberly-Clark Worldwide, Inc.

(57) ABSTRACT

A pull-activated applicator includes a barrel, a pledget, a finger grip, and a deployment element. The pledget includes a withdrawal string and is located within the barrel. The barrel, the pledget, and the deployment element are configured such that application of a force to the deployment element in a first direction deploys the pledget and withdrawal string from the barrel in a second direction generally opposite the first direction.

8 Claims, 34 Drawing Sheets

(51) Int. Cl.
*A61F 13/26* (2006.01)
*A61F 13/551* (2006.01)

(56) References Cited

U.S. PATENT DOCUMENTS

| | | |
|---|---|---|
| 2,401,585 A | 6/1946 | Seidler |
| 2,430,250 A | 11/1947 | Seidler |
| 2,509,241 A | 5/1950 | Mende |
| 3,058,469 A | 10/1962 | Crockford |
| 3,998,225 A | 12/1976 | Hytonen |
| 4,857,044 A | 8/1989 | Lennon |
| 5,080,659 A | 1/1992 | Nakanishi |
| 5,445,605 A | 8/1995 | Pluess |
| 6,156,021 A | 12/2000 | Tojkander |
| 8,734,414 B2 * | 5/2014 | Winkel et al. ............ 604/385.17 |
| 2001/0014784 A1 | 8/2001 | Tweddell et al. |
| 2002/0107497 A1 | 8/2002 | Osborn, III et al. |
| 2004/0127879 A1 * | 7/2004 | Pauley et al. ............ 604/385.18 |
| 2009/0247928 A1 | 10/2009 | Bartning et al. |
| 2009/0247930 A1 | 10/2009 | Fung |

FOREIGN PATENT DOCUMENTS

| | | |
|---|---|---|
| GB | 589111 | 6/1947 |
| RU | 2290156 C2 | 12/2012 |
| WO | WO 2005/041833 A1 | 5/2005 |

* cited by examiner

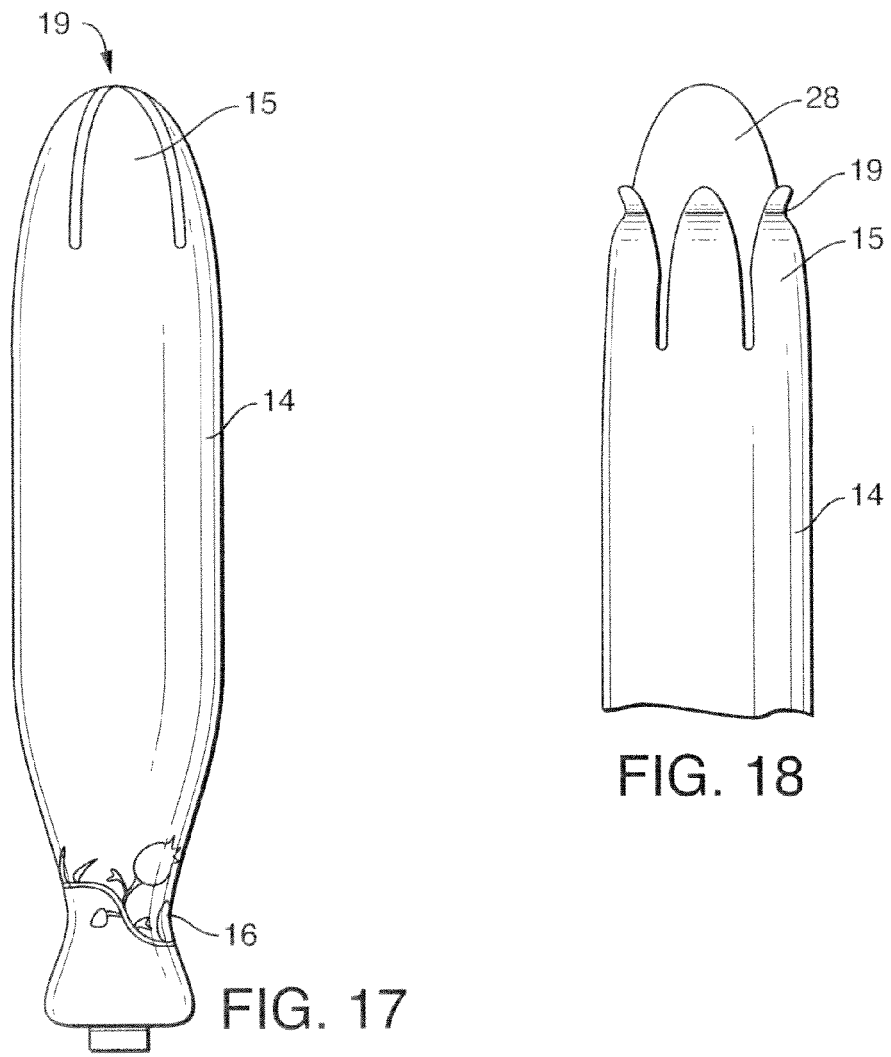
FIG. 17
FIG. 18
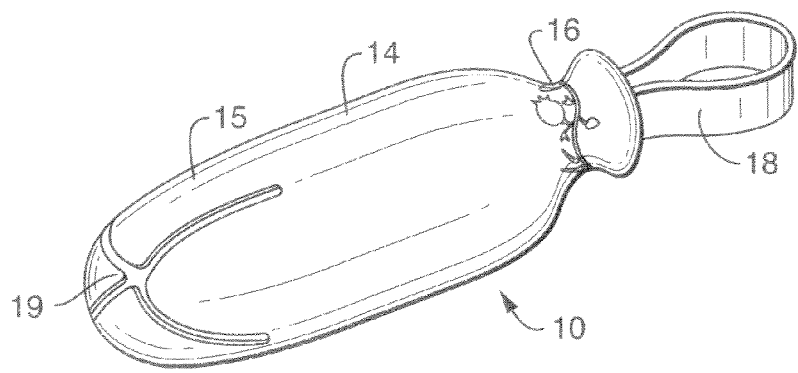
FIG. 19

PULL-ACTIVATED TAMPON APPLICATOR

REFERENCE TO PRIOR APPLICATION

This application claims the benefit of U.S. Provisional Application No. 61/265,248 filed Dec. 17, 2009, and entitled "Pull-Activated Tampon Applicator", and U.S. Non-Provisional application Ser. No. 12/915,224, filed Oct. 29, 2010, and entitled "Pull-Activated Tampon Applicator", the entirety of which is incorporated herein by reference.

BACKGROUND OF THE INVENTION

Traditional tampon applicators have generally included a barrel, a pledget positioned within the barrel, a finger grip, and a plunger. In application, the barrel is positioned within the vaginal canal and force is applied to the plunger in a direction towards the body. As the plunger is pushed into the barrel of the applicator, the pledget is expelled into the vaginal canal. Thus, the pledget generally moves in the same direction the plunger is moved.

Other tampon applicators have utilized a withdrawal string to expel a pledget from a barrel into a body cavity. In these applicators, the withdrawal string extends from the insertion end of the barrel or the side of the barrel and is pulled to expel the pledget. However, these applicators require the withdrawal string to be positioned against the body during insertion of the applicator and expulsion of the pledget. This is undesirable because of possible discomfort, irritation, and friction as the string is moved past the delicate vaginal tissue. Additionally, these applicators exert force on the pledget at the point of attachment between the withdrawal string and the pledget. This configuration is undesirable because the force applied to the withdrawal string may damage or deform the pledget and may cause the withdrawal string to detach during removal of the pledget from the body.

Thus, there is a need for a tampon applicator wherein force is applied in a first direction and the pledget is expelled in a second direction opposite the first direction and wherein the withdrawal string is shielded from the body and protected from damage.

SUMMARY OF THE INVENTION

In one aspect, the present invention provides a pull-activated applicator. The pull-activated applicator includes a barrel, a pledget, a finger grip, and a deployment element. The pledget includes a withdrawal string and the pledget is located within the barrel. The barrel, the pledget, and the deployment element are configured such that application of a force to the deployment element in a first direction deploys the pledget and withdrawal string from the barrel in a second direction generally opposite the first direction.

In some embodiments, the pull-activated applicator may further include a pusher, a first directional transition element, and a second directional transition element. The first directional transition element and the second directional transition element are located within the barrel. The deployment element extends from the finger grip and is mechanically joined to the pusher such that the force applied to the deployment element in the first direction is reversed by the first directional transition element and the second directional transition element and is applied to the pusher in the second direction.

In some embodiments, the barrel of the pull-activated applicator and the finger grip of the pull-activated applicator are formed as two separate pieces and are joined together to define an internal space.

In some embodiments, the pull-activated applicator includes a pledget having an elliptical cross-sectional shape and a barrel having a circular cross-sectional shape.

In some embodiments, the pull-activated applicator includes a deployment element having a stroke length of 40 to 50 mm. In some embodiments, the pull-activated applicator includes a deployment element having an anti-reversing mechanism.

In some embodiments, the pull-activated applicator includes a finger grip having a deployment element opening and a separate withdrawal string opening. The deployment element opening may be elongated, have an elongated direction, and have the deployment element passing there through. The withdrawal string opening may be aligned with the elongated direction and may have the withdrawal string passing there through.

In some embodiments, the pull-activated applicator includes a finger grip having a deployment element opening and a pair of flattened finger grip sides. The deployment element opening is elongated, has an elongated direction, and has the deployment element passing there through. The pair of flattened finger grip sides define a first plane and a second plane that are substantially parallel to each other and to the elongated direction of the deployment element opening.

In some embodiments, the pull-activated applicator includes a deployment element that defines a grasping portion configured as a loop and has a starting loop size of 26 to 90 mm.

In another aspect, the present invention provides a pull-activated applicator having a barrel, a finger grip, a deployment element, a pusher, and a pledget. The barrel and the finger grip define an internal space and the pledget, the pusher, and at least a portion of the deployment element are positioned within the internal space. The applicator has an insertion end opposite a finger grip end. The portion of the deployment element in the internal space defines a deployment element path. The deployment element moves along the deployment element path from the finger grip end towards the insertion end, over a first directional transition element which redirects the deployment element along the deployment element path towards the finger grip end, under the pusher which redirects the deployment element along the deployment element path towards the insertion end, over a second directional transition element which redirects the deployment element along the deployment element path towards the finger grip end.

In some embodiments, the pull-activated applicator includes a pusher that is flattened on opposing sides and the deployment element path passes on the flattened sides.

In some embodiments, the pull-activated applicator includes a first directional transition element and a second directional transition element that include tracking guides.

In some embodiments, the pull-activated applicator includes a deployment element having a stroke length of 40 to 50 mm.

In some embodiments, the pull-activated applicator includes a finger grip and a pledget holder. The pledget holder includes the first directional transition element and the second directional transition element.

In some embodiments, the pull-activated applicator includes a pledget holder having a first slot oriented parallel to a longitudinal centerline and a second slot oriented perpendicularly to the longitudinal centerline.

In some embodiments, the pull-activated applicator includes a pusher having an energy director at the point of attachment with the deployment element.

In another aspect, the present invention provides a pull-activated applicator having a barrel, a pledget, a pusher, a finger grip, a first directional transition element, a second directional transition element, and a deployment element. The barrel defines an insertion end having a plurality of petals. The finger grip defines a finger grip end and includes a deployment element opening and a separate withdrawal string opening proximate the finger grip end. The deployment element defines a reserve portion and a grasping portion and passes through the deployment element opening. The finger grip and the barrel are joined together to define an internal space. The internal space includes the pledget, the pusher, the directional transitional elements, and the reserve portion of the deployment element. The pledget has a first end positioned proximate the plurality of petals and a second end positioned proximate the pusher. The pledget includes a withdrawal string and the withdrawal string passes through the withdrawal string opening. The deployment element may define a deployment element path. The deployment element path defines a point of beginning where the deployment element passes into the interior space. The deployment element moves along the deployment element path from the point of beginning to the first directional transition element which redirects the deployment element along the deployment element path towards the finger grip end, under the pusher which redirects the deployment element along the deployment element path towards the insertion end, over the second directional transition element which redirects the deployment element along the deployment element path towards the finger grip end, and out of the interior space.

In some embodiments, the pull-activated applicator includes a deployment element made from woven polyester filaments. In some embodiments, the pull-activated applicator includes a deployment element made with a satin weave and has pressure bonded side edges.

In some embodiments, the pull-activated applicator may include a deployment element that defines a grasping portion that is configured as a loop. In some embodiments, the deployment element may have a starting loop size of 26 to 90 mm and a finished loop size of 100 to 184 mm.

BRIEF DESCRIPTION OF THE DRAWINGS

FIG. 17 is a side view of a barrel having a dip tip.

FIG. 18 is a side view of a barrel having a dip tip and a partially expelled pledget.

FIG. 19 is a perspective view of a barrel having a dip tip.

DETAILED DESCRIPTION OF THE DRAWINGS

The present invention provides a more streamlined and sleek tampon applicator having a unique delivery mechanism. The delivery mechanism allows for force to be applied to a deployment element in a direction away from the body and the tampon pledget to be expelled in a direction towards the body. This delivery system is believed to be more comfortable and less intimidating to use as compared to traditional plunger style tampon applicators.

As discussed above, some prior art devices have utilized the withdrawal string as a means for expelling the pledget from the applicator. While not wishing to be bound by theory, it is believed that utilizing a separate deployment element as opposed to the withdrawal string is advantageous for several reasons. First, utilizing a separate deployment element provides more controlled placement of the pledget within the body cavity because the deployment element can be designed with a greater width than the withdrawal string and thus will have greater contact with either the pledget or the pusher during deployment. Furthermore, there is less chance that the user will dislodge or remove the pledget from the body cavity when removing the pull-activated applicator because the deployment element remains with the pull-activated applicator and the withdrawal string remains with the pledget after deployment. Additionally, using the deployment element to expel the pledget instead of the withdrawal string may decrease the chances of damaging the connection between the withdrawal string and the pledget and therefore reduce the chances of failure during use or removal. Likewise, using a separate deployment element and withdrawal string allows for both elements to be sized and shaped for their specific and different functions. Specifically, the deployment element may be significantly longer than would be desirable for a withdrawal string that must remain extending from the body of the user. Finally, utilizing a separate deployment element allows for specific and different materials to be selected for both the deployment element and the withdrawal string. This allows for specialized material choices for the deployment element because the deployment element does not contact the body of the user or remain in proximity to the body of the user like a withdrawal string does. Likewise, this allows for specialized material choices for the withdrawal string because the withdrawal string does not have to have the strength, control, or feel like the deployment element does. Thus, the deployment element can, for example, include optical brightners, metallic finishes, perfumes, inks, nano-components, microencapsulated components, and other materials that may not be suitable for use with withdrawal strings.

Figure 1:
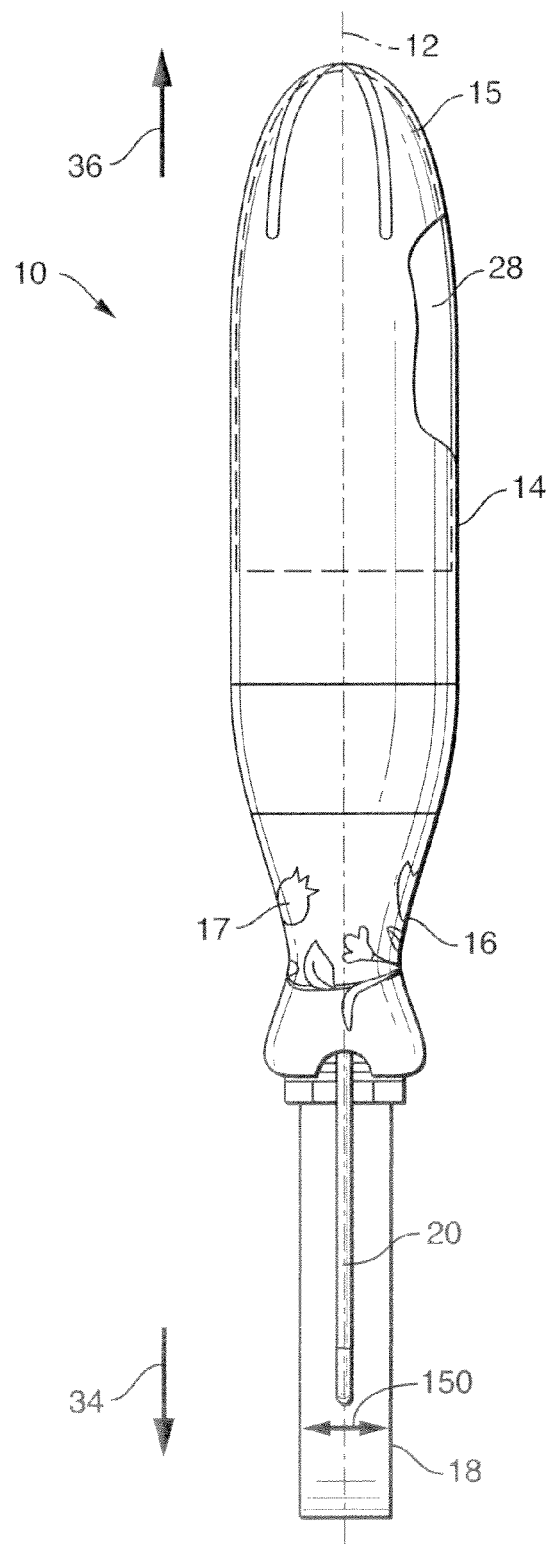
FIG. 1 is a first side view of an exemplary pull-activated applicator.
Figure 2:
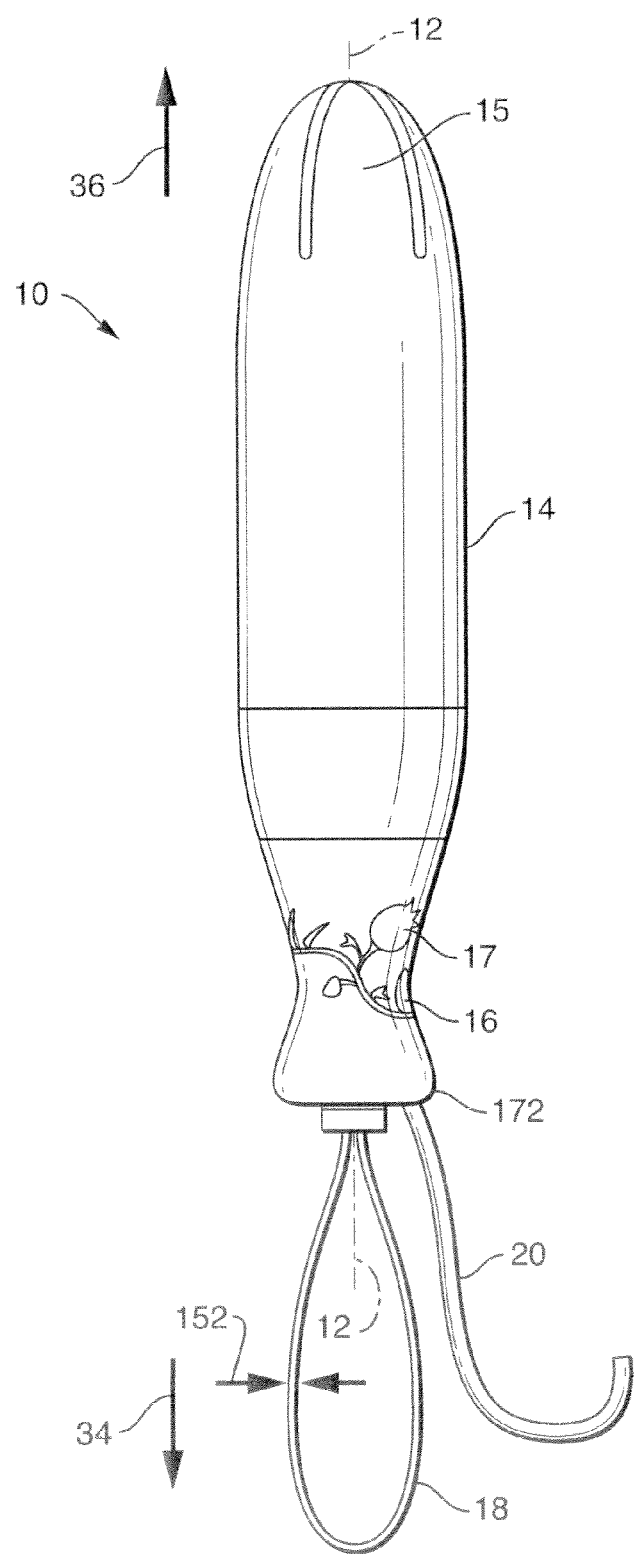
FIG. 2 is a second side view, rotated 90 degrees along the longitudinal centerline, of the pull-activated applicator of FIG. 1.
Figure 3:
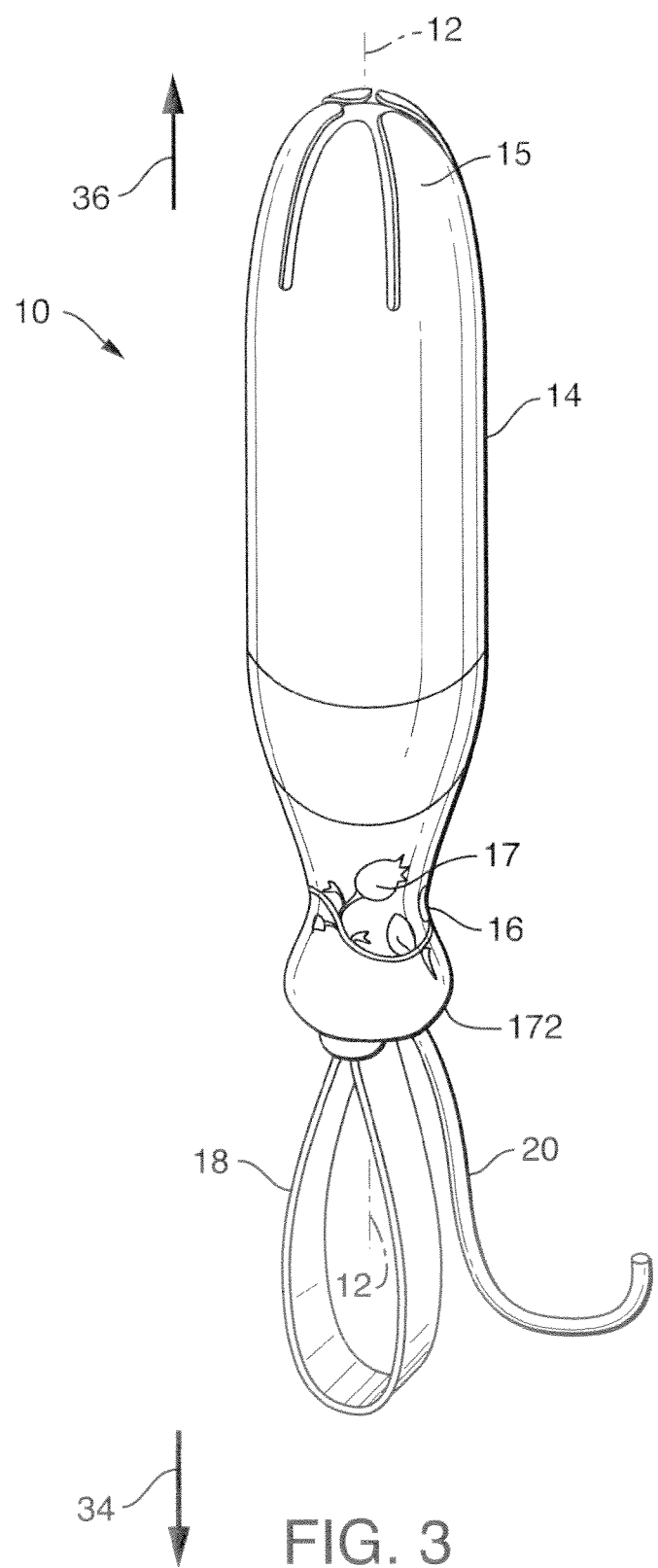
FIG. 3 is a third side view, rotated along the longitudinal centerline, of the pull-activated applicator of FIG. 1.
Figure 4:
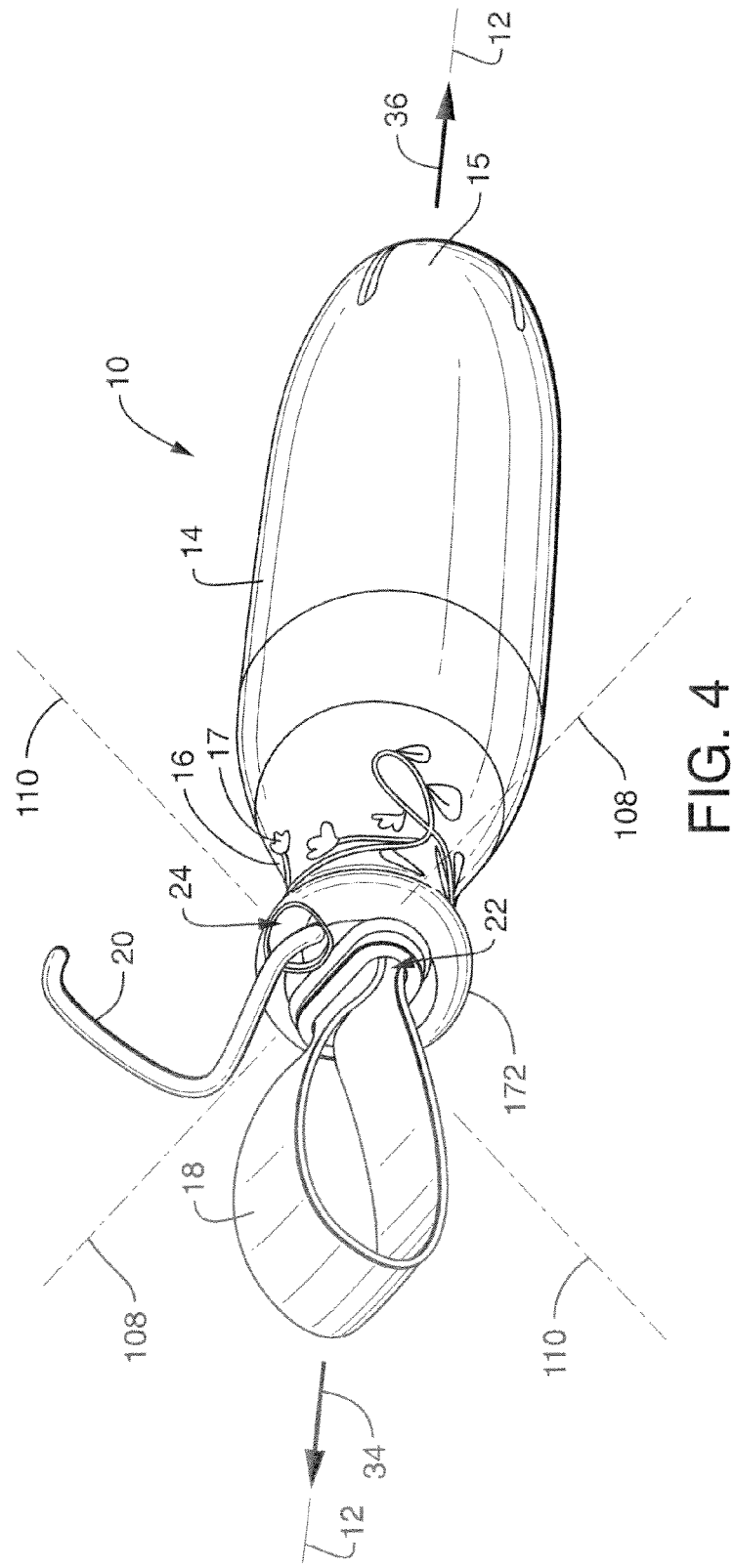
FIG. 4 is a bottom perspective view of the pull-activated applicator of FIG. 1.

FIG. 1 is a first side view of an exemplary pull-activated applicator 10 with portions cut away to illustrate internal components. FIG. 2 is a second side view, rotated 90 degrees around a longitudinal centerline 12, of the pull-activated applicator 10 of FIG. 1. FIG. 3 is a third side view, rotated along the longitudinal centerline 12, of the pull-activated applicator 10 of FIG. 1. FIG. 4 is a bottom perspective view of the pull-activated applicator 10 of FIG. 1.

Referring now to FIGS. 1-4, the pull-activated applicator 10 includes a longitudinal centerline 12, a barrel 14, a finger grip 16, and a deployment element 18. The pull-activated applicator 10 also includes a pledget 28 located therein. The pledget 28 may include a withdrawal string 20. The pull-activated applicator 10 may include a deployment element opening 22 and may include a withdrawal string opening 24 as illustrated in FIG. 4. The barrel 14, the pledget 28, and the deployment element 18 are configured such that application of a force to the deployment element 18 in a first direction 34 deploys the pledget 28 and the withdrawal string 20 from the barrel 14 in a second direction 36 generally opposite the first direction 34. However, one skilled in the art will readily appreciate that application of pulling force to the deployment element 18 in any other direction will also provide deployment of the pledget 28 and the withdrawal string 20 from the barrel 14 in the second direction 36.

Figure 5:
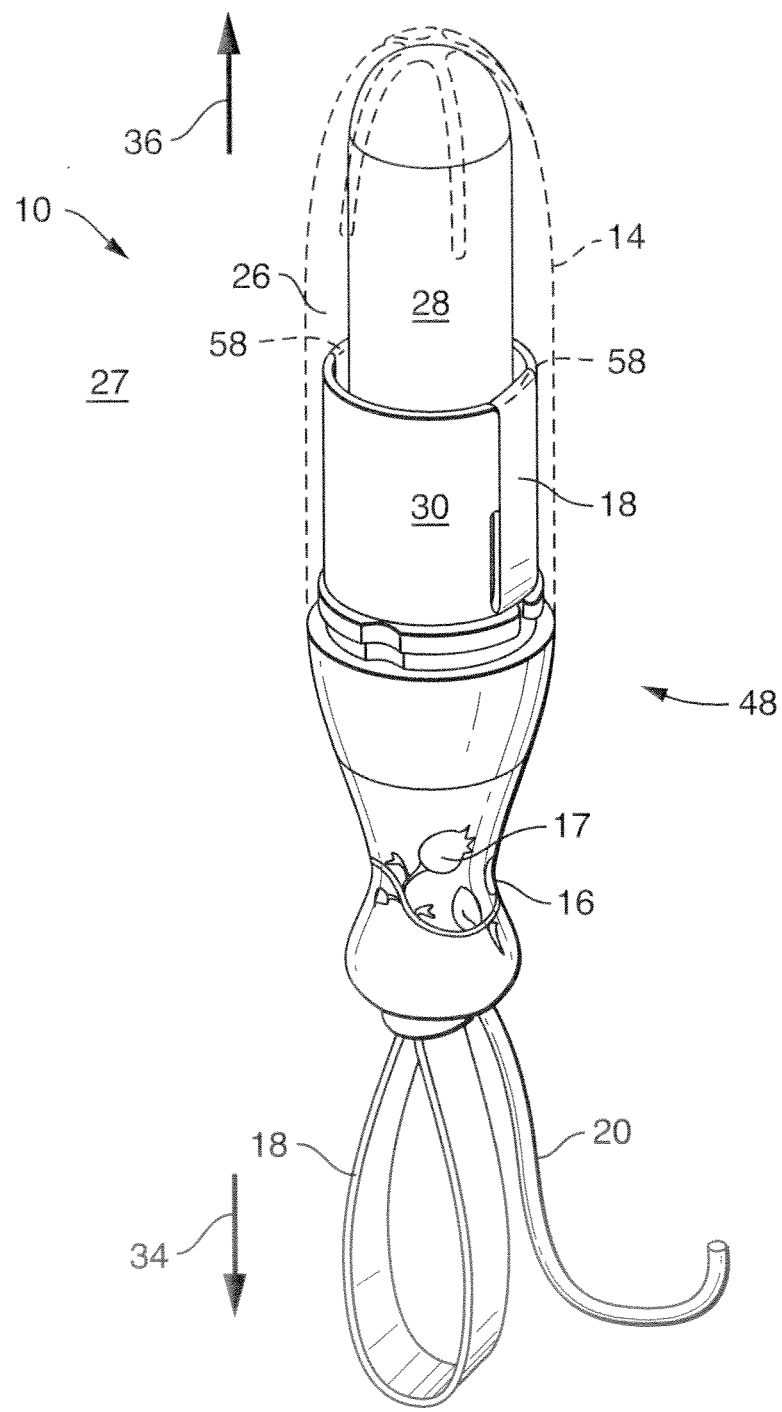
FIG. 5 representatively illustrates the pull-activated applicator of FIG. 3 with portions shown in phantom to illustrate internal structure.
Figure 6:
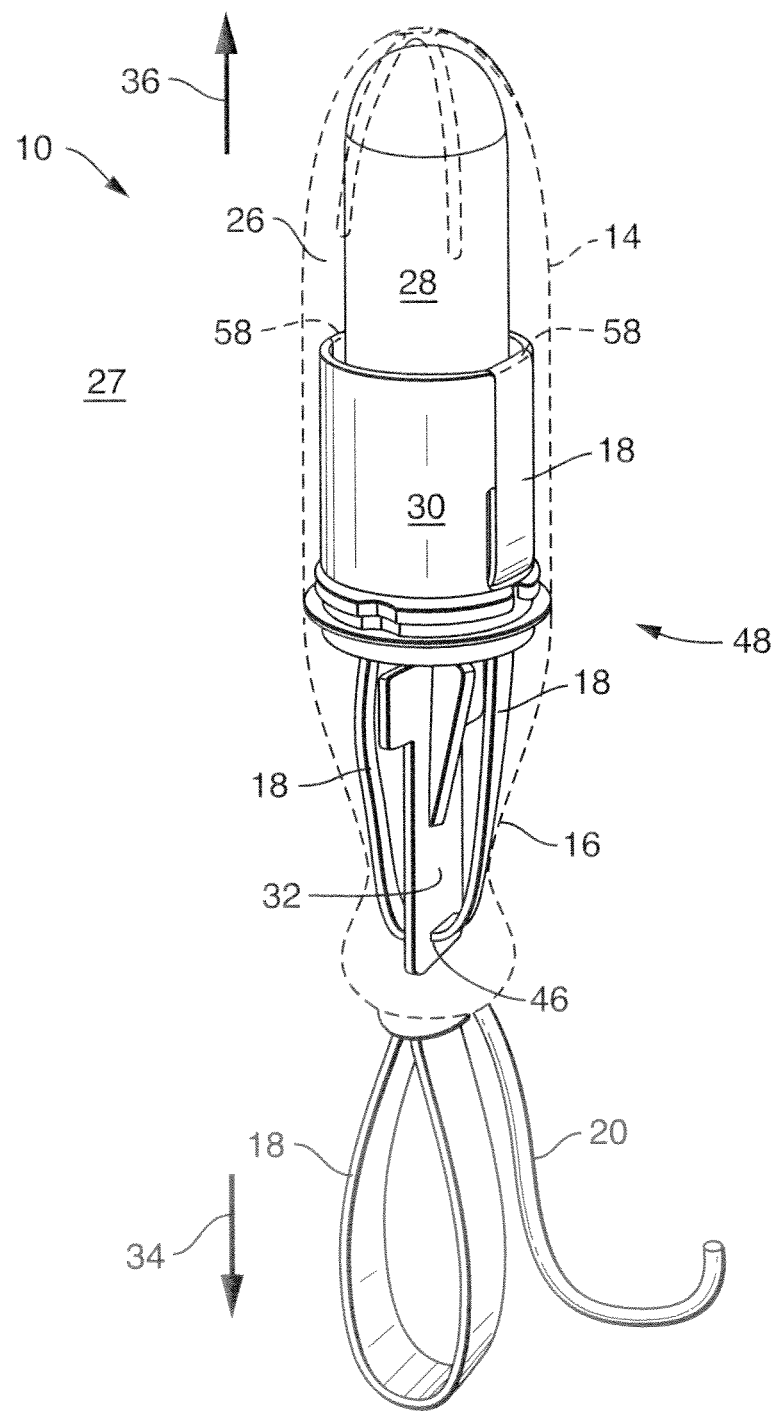
FIG. 6 is a side perspective view of an exemplary pull-activated applicator with portions shown in phantom to illustrate internal structure.
Figure 7:
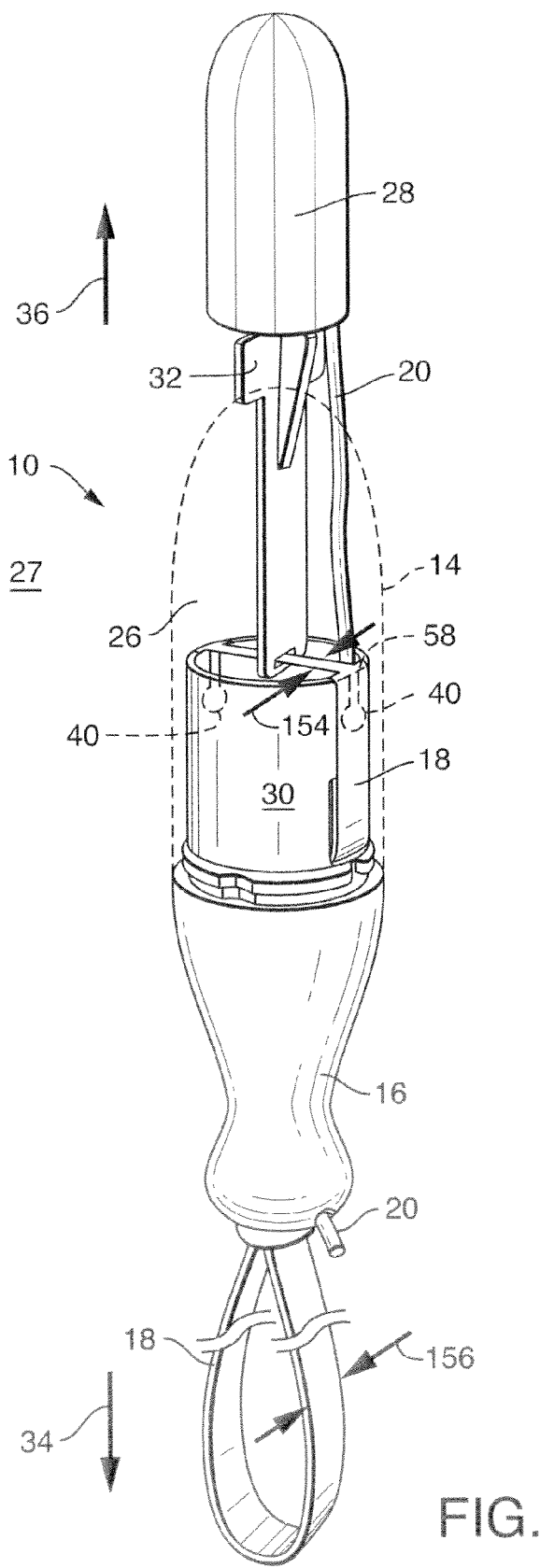
FIG. 7 is a side perspective view of an exemplary pull-activated applicator with portions shown in phantom to illustrate internal structure and an expelled tampon pledget.

Referring now to FIGS. 5, 6, and 7, an exemplary pull-activated applicator 10 is illustrated with a barrel 14 drawn in phantom lines to illustrate internal components and structure. Likewise, FIG. 6 also includes the finger grip 16 drawn in phantom lines to illustrate internal structure. The pull-activated applicator 10 of FIGS. 5-7 defines an internal space 26 and an external space 27. The internal space 26 initially includes a pledget 28. In various embodiments, the internal space 26 may also include a pledget holder 30 and/or a pusher 32 located therein as illustrated in FIG. 6.

The internal space 26 of the pull-activated applicator 10 also includes one or more directional transition elements 58. The directional transition elements 58 may be any suitable structure that redirects force applied to the deployment element 18 from a first direction 34 to a second direction 36 wherein the second direction 36 is different than the first direction 34. The directional transition elements 58 are located within the internal space 26 and generally include rounded edges to minimize drag as the deployment element 18 moves over the directional transition elements 58 during assembly and deployment.

FIGS. 5 and 6 illustrate the pull-activated applicator 10 in pre-deployment condition 48. In other words, the pull-activated applicator 10 of FIGS. 5 and 6 is ready for use. In this condition, the pull-activated applicator 10 may be inserted into a body cavity such as the vaginal canal. When the user is ready to deploy the pledget 28 into the vaginal canal, force is applied to the deployment element 18 in the direction indicated by the arrow 34. As force is applied to the deployment element 18 in the direction 34 the deployment element 18 applies force in the opposite direction to the pusher 32 (FIG. 6) which in turn moves the pledget 28 in the direction indicated by arrow 36 as illustrated in FIG. 7. FIG. 7 is a side perspective view of the pull-activated applicator 10 with the barrel 14 drawn in phantom lines and the pledget 28 expelled from the barrel 14 in the direction 36.

Figure 8:
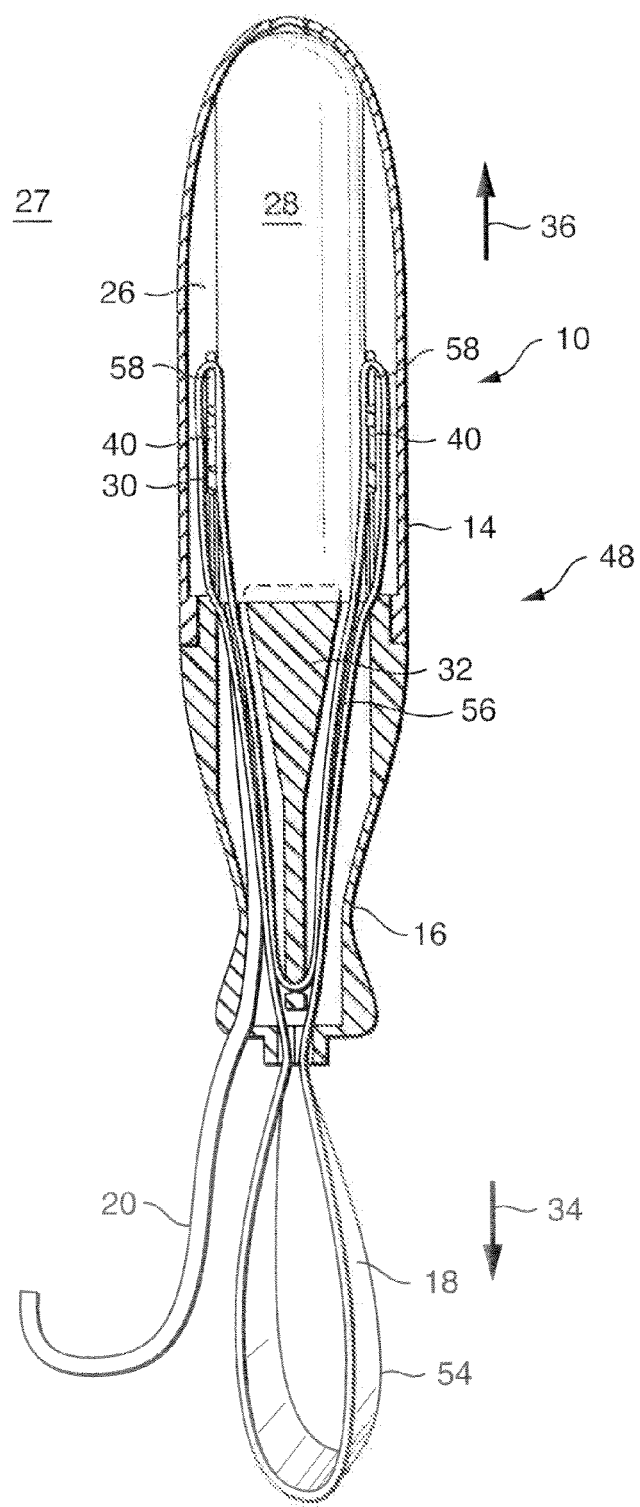
FIG. 8 is a cross-sectional view of an exemplary pull-activated applicator in a pre-deployment condition.
Figure 9:
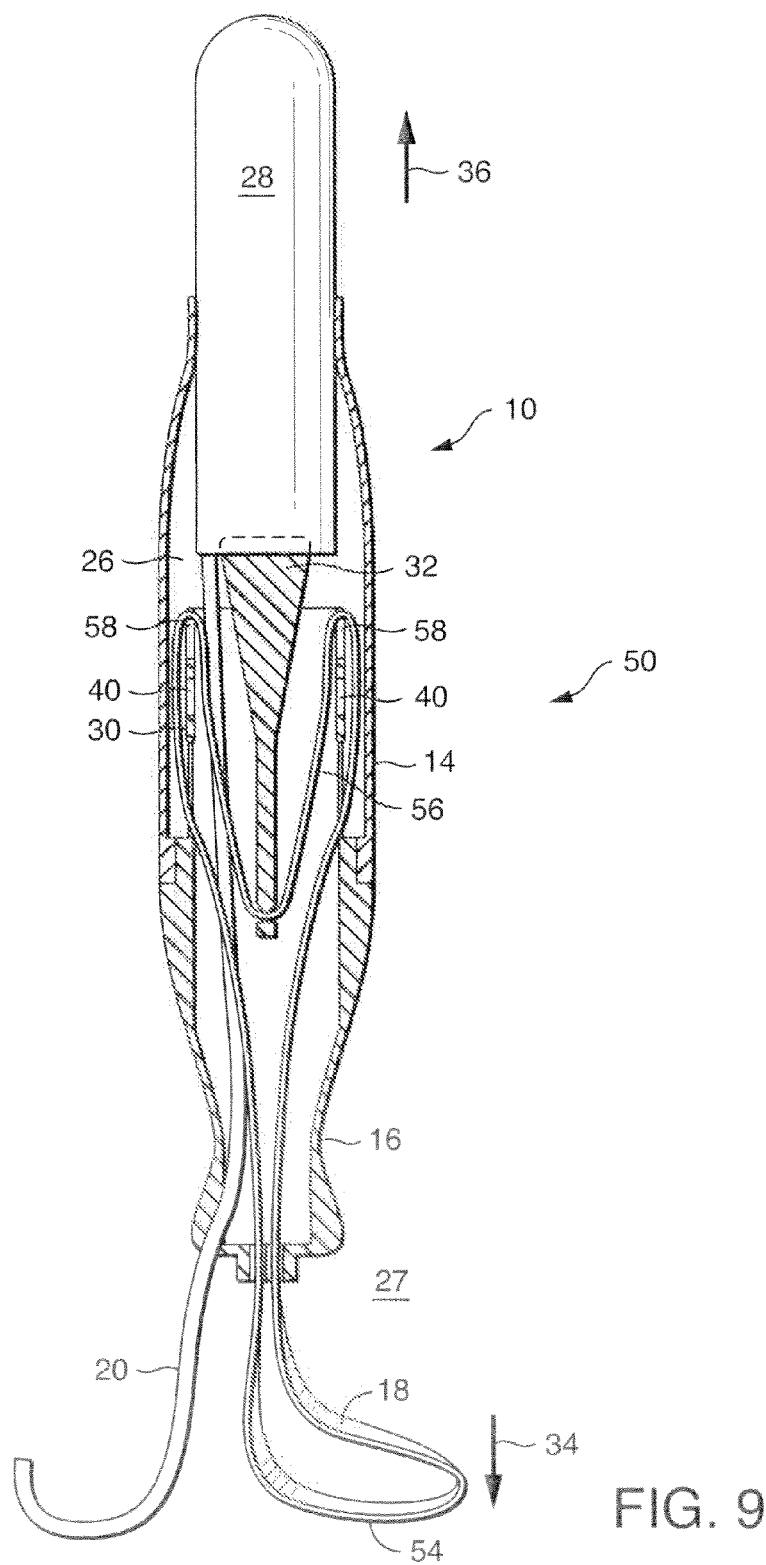
FIG. 9 is a cross-sectional view of the pull-activated applicator of FIG. 8 in a deploying condition.
Figure 10:
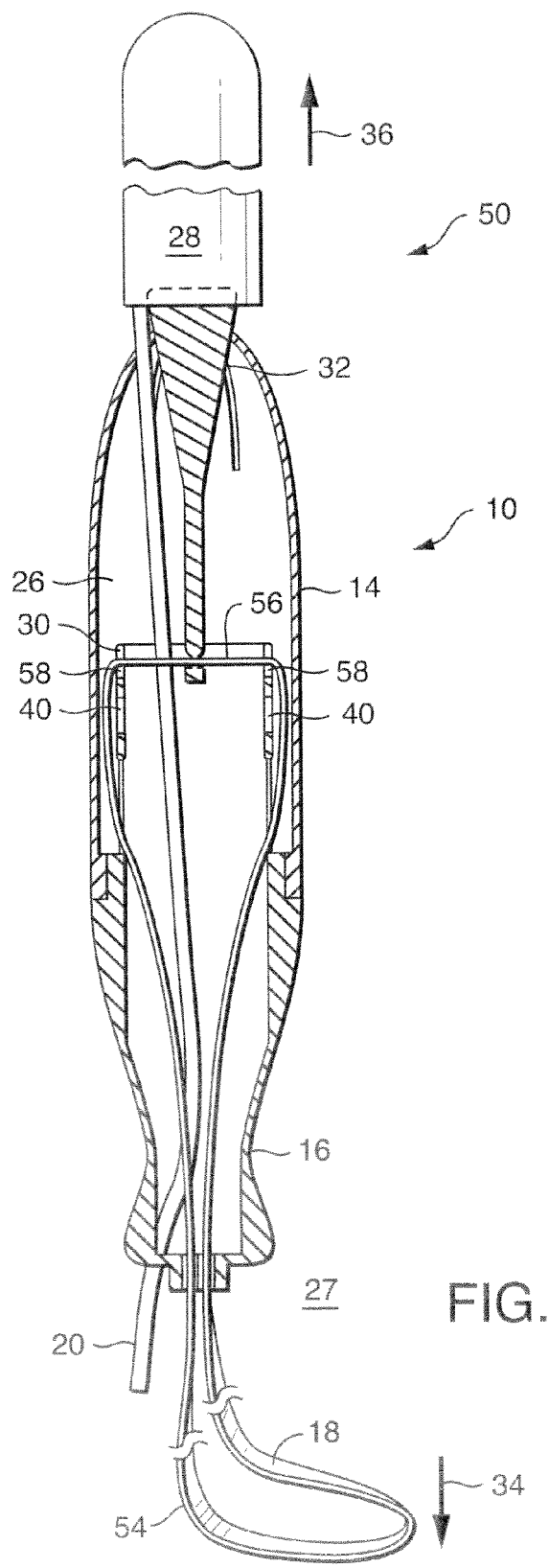
FIG. 10 is a cross-sectional view of the pull-activated applicator of FIG. 8 in a deploying condition.
Figure 11:
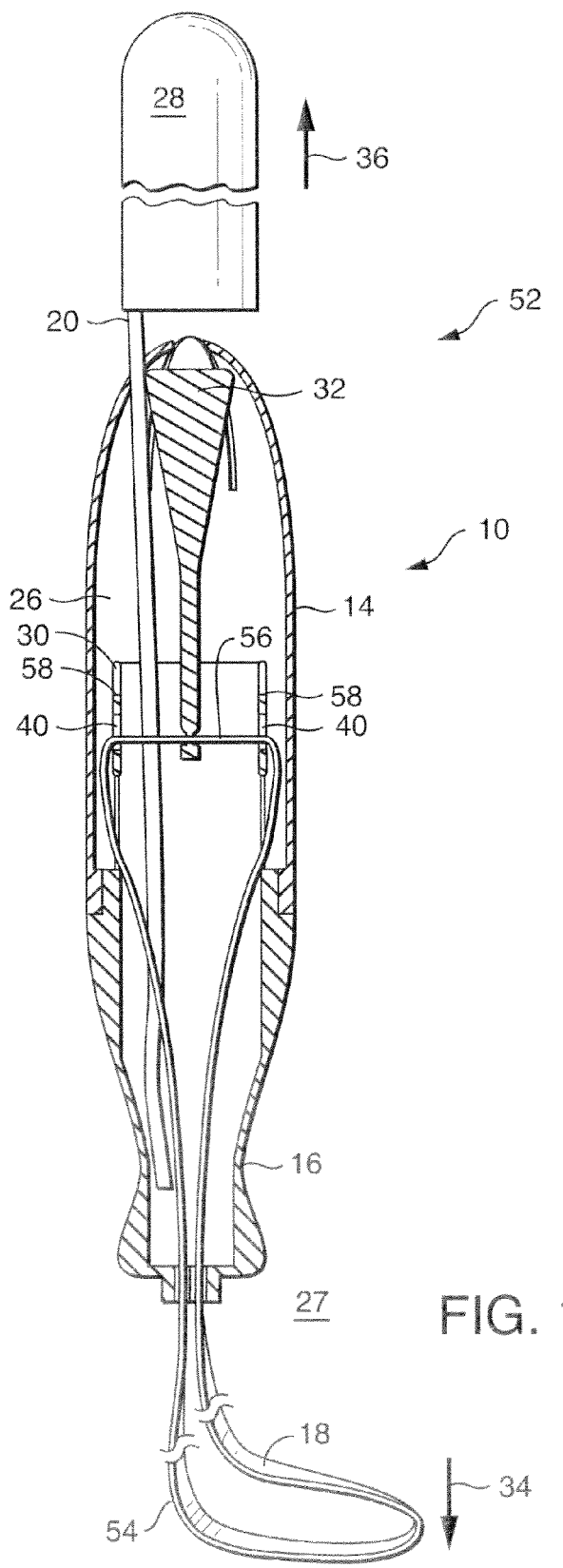
FIG. 11 is a cross-sectional view of the pull-activated applicator of FIG. 8 in a deployed condition.

Referring now to FIGS. 8-11, a cross sectional view of another exemplary pull-activated applicator 10 is illustrated. FIG. 8 is a cross-sectional view of the exemplary pull-activated applicator 10 in a pre-deployment condition 48. FIG. 9 is a cross-sectional view of the pull-activated applicator 10 of FIG. 8 in a deploying condition 50. FIG. 10 is a cross-sectional view of the pull-activated applicator 10 of FIG. 8 in a deploying condition 50. Finally, FIG. 11 is a cross-sectional view of the pull-activated applicator 10 of FIG. 8 in a deployed condition 52. As can be seen in FIG. 11, the deployment element 18 has engaged the key holes 40 upon complete deployment of the pledget 28.

In the pre-deployment condition 48, as illustrated in FIG. 8, the deployment element 18 defines a grasping portion 54 and a reserve portion 56. The grasping portion 54 is generally the portion of the deployment element 18 that starts in the external space 27 and is engaged by the user to deploy the pledget 28. The reserve portion 56 is generally that portion of the deployment element 18 that starts in the internal space 26 and extends from the directional transition element 58 to the pusher 32 and back to the other directional transition element 58.

In the pre-deployment condition 48, the user applies force in the direction 34 to the grasping portion 54 of the deployment element 18 of the pull-activated applicator 10 as illustrated in FIG. 8. The force applied in the direction 34 causes the reserve portion 56 to be drawn over the directional transitional elements 58 which in turn causes force to be applied to the pusher 32 in the direction 36 as illustrated in FIG. 9. As force is continued in the direction 34, the reserve portion 56 of the deployment element 18 continues to shorten causing the pusher 32 to continue to move in the direction 36 and continue to expel the pledget 28 from the internal space 26 of the pull-activated applicator 10 as illustrated in FIG. 10. Finally, the reserve portion 56 of the deployment element 18 is pulled taut across directional transition element 58 as illustrated in FIG. 10. In embodiments that include key holes 40, the reserve portion 56 is pulled taut across the directional transition element 58 before snapping down into the key holes 40 as illustrated in FIG. 11.

Figure 12:
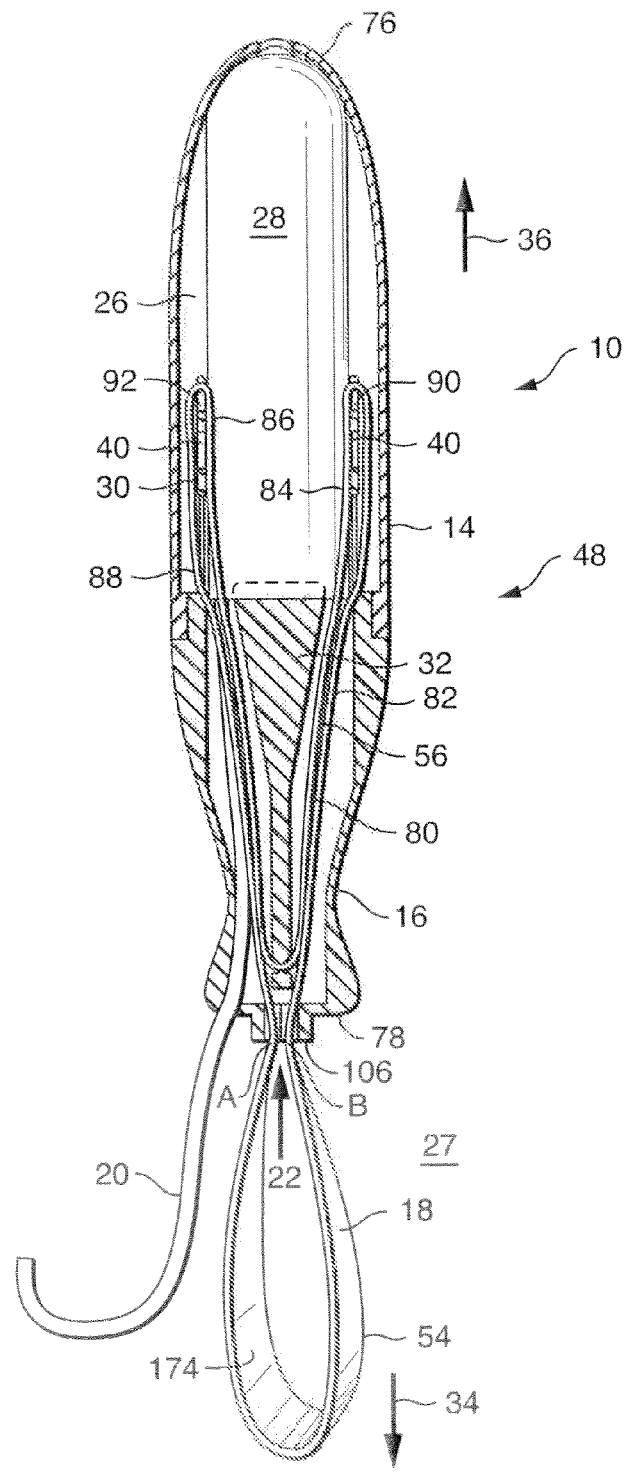
FIG. 12 is a cross-sectional view of an exemplary pull-activated applicator in a pre-deployment condition.

Referring now to FIG. 12, a cross sectional view of another exemplary pull-activated applicator 10 is illustrated. The pull-activated applicator 10 includes a barrel 14, a finger grip 16, a deployment element 18, a pusher 32, and a pledget 28. The barrel 14 is joined with the finger grip 16 to define an internal space 26. The pledget 28, the pusher 32, and at least a portion of the deployment element 18 are positioned within the internal space 26. The barrel 14 has an insertion end 76 opposite a finger grip end 78. The portion of the deployment element 18 in the internal space 26 defines a deployment element path 80. A first portion 82 of the deployment element path 80 extends the deployment element 18 from the finger grip end 78 (point of beginning 106) towards the insertion end 76 to a first directional transition element 90. The deployment element 18 extends over the first directional transition element 90 which redirects the deployment element 18 along a second portion 84 of the deployment element path 80 towards the finger grip end 78. The deployment element 18 extends under or through the pusher 32 which redirects the deployment element 18 along a third portion 86 of the deployment element path 80 towards the insertion end 76. The deployment element 18 extends over a second directional transition element 92 which redirects the deployment element 18 along a fourth portion 88 of the deployment element path 80 towards the finger grip end 78. Upon exiting the internal space 26, the deployment element 18 may have any suitable configuration, such as, for example, a loop connecting back to the deployment element 18 at the point of beginning 106.

As can be seen in FIG. 12, both the first directional transition element 90 and the second directional transition element 92 may also include keyholes 40. The keyholes 40 are configured to become part of the deployment element path 80 after the deployment element 18 has been fully extended and the pledget 28 has been fully deployed as illustrated in FIG. 11.

Figure 13:
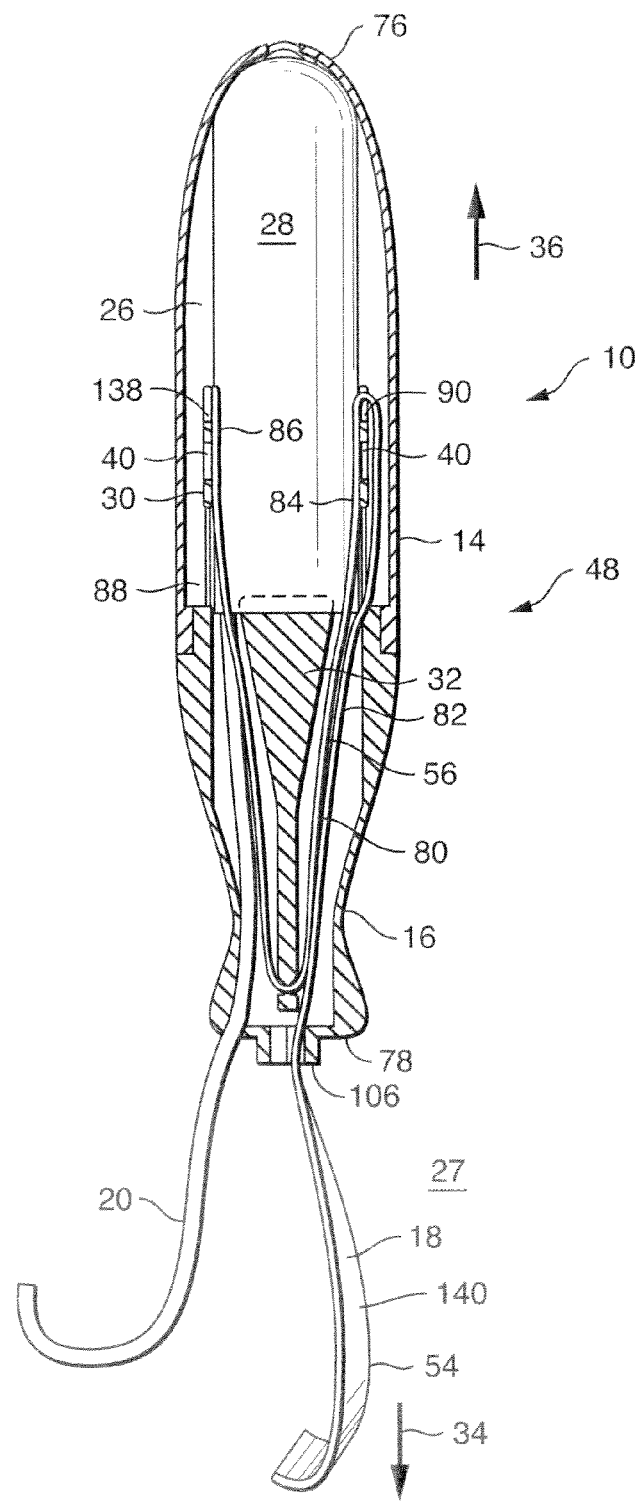
FIGS. 13-16 representatively illustrate alternative deployment element paths and deployment element configurations.

As can be seen in the previous example, the deployment element may be essentially a loop that moves across two directional transition elements during deployment. However, in some embodiments, the deployment element may be fixed within the internal space and move over a single deployment element. For example, the deployment element 18 may be joined to the pledget holder 30, the barrel 14, and/or the finger grip 16. Referring now to FIG. 13, a cross sectional view of another exemplary pull-activated applicator 10 is illustrated. The pull-activated applicator 10 includes a barrel 14, a finger grip 16, a deployment element 18, a pusher 32, and a pledget 28. The barrel 14 is joined with the finger grip 16 to define an internal space 26. The pledget 28, the pusher 32, and at least a portion of the deployment element 18 are positioned within the internal space 26. The barrel 14 has an insertion end 76 opposite a finger grip end 78. The portion of the deployment element 18 in the internal space 26 defines a deployment element path 80. A first portion 82 of the deployment element path 80 extends from the finger grip end 78 towards the insertion end 76 to a first directional transition element 90. The deployment element 18 extends over the first directional transition element 90 which redirects the deployment element 18 along a second portion 84 of the deployment element path 80 towards the finger grip end 78. The deployment element 18 extends under or through the pusher 32 which redirects the deployment element 18 along a third portion 86 of the deployment element path 80 towards the insertion end 76. The deployment element 18 extends to and joins with a fixed point 138 thereby terminating the deployment element path 80. The fixed point 138 may be any suitable point in the internal space 26. For example, as illustrated in FIG. 13, the fixed point 138 may be a portion of the pledget holder 30. In other embodiments, the fixed point 138 may be joined with the barrel 14 and/or the finger grip 16.

In the embodiment illustrated in FIG. 13, a user applies force in the direction 34 to the grasping portion 54 of the deployment element 18 of the pull-activated applicator 10 which causes the reserve portion 56 to be drawn over the transitional element 90 which in turn applies force to the pusher 32 in the direction 36. As force continues to be applied in the direction 34, the reserve portion 56 of the deployment element 18 continues to shorten causing the pusher 32 to continue to move in the direction 36 and continue to expel the pledget 28 from the internal space 26 of the pull-activated applicator 10. Finally, the reserve portion 56 of the deployment element 18 is pulled taut between the first directional transition element 90 and the fixed point 138. In these and other embodiments, the pusher 32 and the deployment element 18 may be joined together such that the deployment element 18 can slide beneath or through the pusher 32 while applying force in the direction 36.

Figures 14, 15, 16:
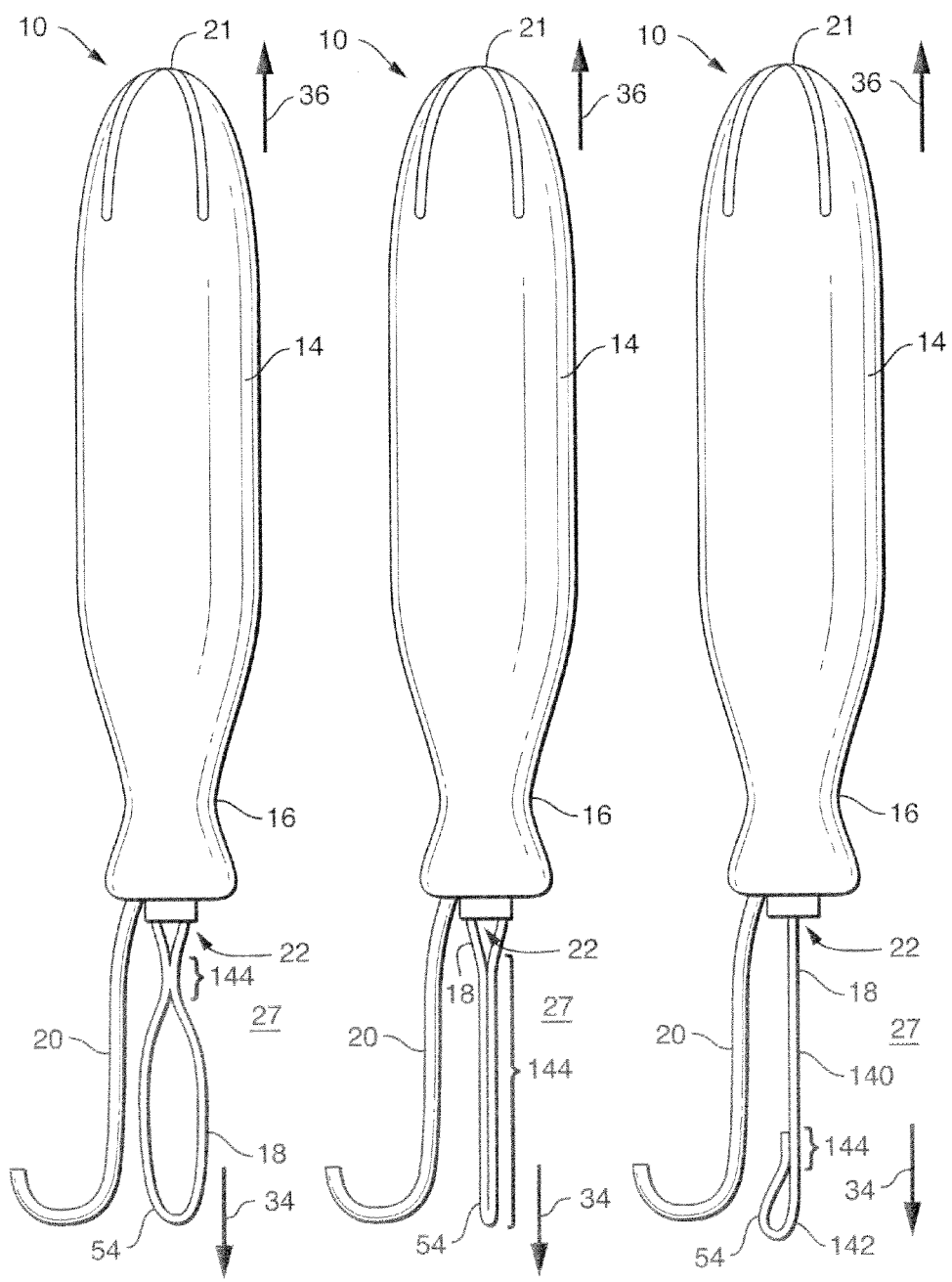

In various embodiments, the pull-activated applicator 10 may include any suitable deployment element path 80 through the internal space 26. Likewise, upon exiting the internal space 26, the deployment element 18 may include any suitable configuration in the external space 27. For example, as illustrated in FIG. 12, the deployment element 18 may be configured as a loop in the external space 27. In other embodiments, the deployment element 18 may be configured as a unitary pull 140, as illustrated in FIG. 13. In yet other embodiments, the deployment element 18 may be configured as a loop with portions 144 joined together as illustrated in FIGS. 14 and 15. Alternatively, the deployment element 18 may be configured as a unitary pull 140 with a portion joined to itself to define a unitary pull loop 142 as illustrated in FIG. 16.

In various embodiments, the barrel 14 provides a smooth structure to ease insertion of the pull-activated applicator 10 into a body cavity. The barrel 14 defines an insertion end 21 that may have any suitable shape or taper. For example, the insertion end 21 of the barrel 14 may have a generally elongated taper for increased comfort.

The barrel 14 may be made of any suitable materials such as low density polyethylene, thermoplastic elastomer, cardboard, foam, or the like, or combinations thereof. In some embodiments, the barrel 14 may be made with an injection molded thermoplastic, such as low density polyethylene. In various embodiments, the barrel 14 may include any suitable number of petals 15 of any suitable length. In some embodiments, the barrel 14 may include five petals 15 having a length of 15 mm or greater. The petals 15 may be shaped in any suitable configuration and may include a dip tip 19 as illustrated in FIGS. 17, 18, and 19. The petals 15 generally provide for comfortable insertion of the applicator and flex to allow the pledget 28 to be expelled with minimal resistance. The petals 15 may be molded into final shape during the formation of the barrel 14 or may be shaped in a separate process. The petals 15 may be shaped using any suitable method such as thermal shaping or mechanical shaping. The pledget 28 may be inserted into the barrel 14 before shaping the petals 15 or after shaping the petals 15. In some embodiments, the barrel 14 may not include any petals 15 and may be open on the insertion end 21. Additionally, the barrel 14 may have a relatively blunt insertion end 21 in various embodiments, Referring now to FIG. 17, a side view of an exemplary barrel 14 integrated with an exemplary finger grip 16 is illustrated. The barrel 14 includes petals 15 having a dip tip 19. The dip tip 19 is indented into the end of the barrel 14 to provide a smoother surface and reduce the likelihood of pinching during insertion. FIG. 18 illustrates the barrel 14 of FIG. 17 as the pledget 28 is expelled. As the force is applied to the pledget 28 the petals 15 flex to allow the pledget 28 to be expelled from the barrel 14. FIG. 19 is a perspective view of a pull-activated applicator 10 having a barrel 14 that includes petals 15 and a dip tip 19. The barrel 14 is illustrated as an integral piece with the finger grip 16 but may also be two separate pieces joined together as discussed herein.

Suitable barrels 14 may include the mechanical properties, surface properties, configurations, and other aspects of those found in U.S. publication 2010/0016780 to VanDenBogart, the entirety of which is incorporated herein by reference where not inconsistent.

The finger grip 16 provides a portion of the pull-activated applicator 10 that is adapted to be grasped by the user during insertion, expulsion, and/or removal of the pull-activated applicator 10. The finger grip 16 may be made of any suitable materials such as thermoplastic low density polyethylene, cardboard, thermoplastic elastomer, foam, or the like, or combinations thereof. In some embodiments, the finger grip 16 may be an injection molded thermoplastic, a thermoplastic elastomer, or combinations thereof. In various embodiments, the finger grip 16 may include one or more gripping elements 17, as illustrated, for example, in FIGS. 1-4. The gripping elements 17 may be made of any suitable material such as thermoplastic elastomer and may have any suitable shape. The gripping elements 17 may be formed during the formation of the finger grip 16 or may be added in a separate process. For example, the finger grip 16 and the gripping elements 17 may be formed in a two-shot injection molding process wherein the first shot forms the bulk of the finger grip 16 and the second shot provides the gripping elements 17.

In some embodiments, the finger grip 16 may be molded with a decorative portion set in a gripper material. For example, the finger grip 16 may be made of a base material and a soft gripper material. The soft gripper material may be a thermoplastic elastomer, foam, or other suitable material. The soft gripper material may be uniformly molded or printed over the base material. In some embodiments, the base material may have raised protrusions and the soft grip material may surround the raised protrusions such that the level of the soft gripper material is approximately level with the raised protrusions thereby creating a level outer gripping surface having differing textures. Other suitable finger grips 16 may include the mechanical properties, surface properties, configurations, and other aspects of those found in U.S. application 2010/0016780 to VanDenBogart. Additionally, in some embodiments, any suitable tackifier may be incorporated into or on the polymers used in the finger grip 16 and/or the gripping elements 17. For example, tackifying resins may be added to increase the coefficient of friction on portions of or all of the finger grip 16 and/or the gripping elements 17.

In some embodiments, the finger grip 16 may be made of pigmented polypropylene and may include gripping elements 17 made of polypropylene. In some embodiments the forming process may include injection molding the gripping elements 17 in the same process that forms the finger grip 16. The gripping elements 17 may extend any suitable distance from the surface of the finger grip 16. In some embodiments, the gripping elements 17 may extend about 0.2 mm from the surface of the grip 16. In other embodiments, the gripping elements 17 may be recessed from the surface of the finger grip 16.

Figure 20:
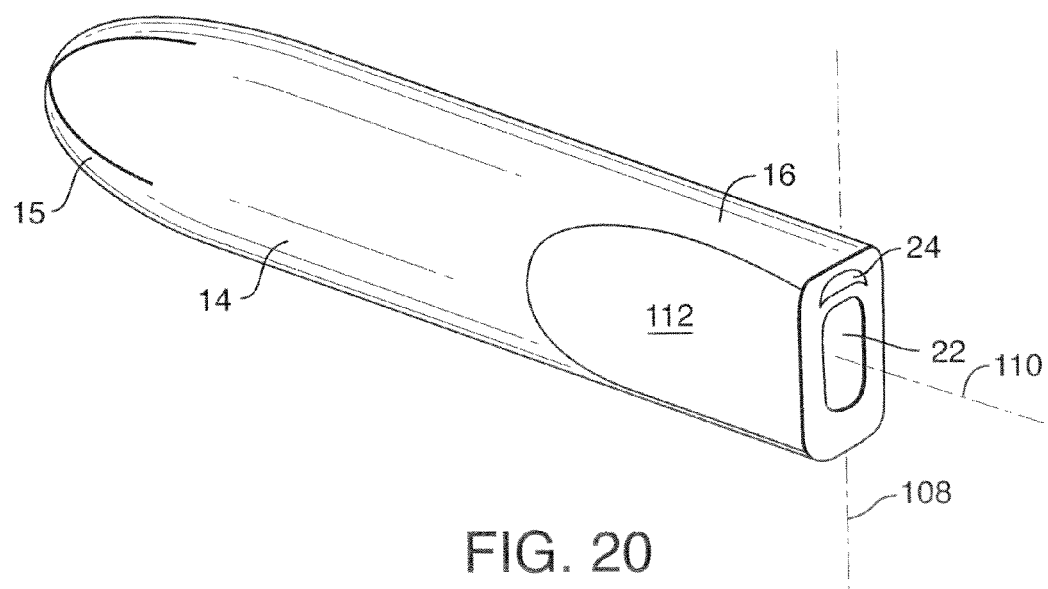
FIG. 20 is a side perspective view of an exemplary barrel and finger grip.

The finger grip 16 also includes at least one opening for the deployment element 18 to pass through. In some embodiments, the withdrawal string 20 may also pass through the same opening as the deployment element 18. However, in some embodiments, the finger grip 16 includes a deployment element opening 22 and a separate withdrawal string opening 24 as illustrated in FIGS. 4 and 20. The deployment element opening 22 and the withdrawal string opening 24 may be any suitable shape or size and may have any suitable relative orientation. For example, the deployment element opening 22 and the withdrawal string opening 24 may be generally circular, semi-circular, oval, elongated, elliptical, square, rectangular, irregular, and the like, and combinations thereof. In a specific example, the deployment element opening 22 may have a generally elongated shape and the withdrawal string opening 24 may have a generally circular shape as illustrated in FIG. 4.

In some embodiments, the finger grip 16 may include an elongated deployment element opening 22 having an elongated direction 108 and a withdrawal string opening 24 aligned in a direction 110 which is perpendicular to the elongated direction 108 as illustrated in FIG. 4. In other embodiments, the finger grip 16 may include an elongated deployment element opening 22 having an elongated direction 108 and a withdrawal string opening 24 aligned with the elongated direction 108 of the deployment element opening 22 as illustrated in FIG. 20.

In some embodiments, the finger grip 16 may include flattened finger grip sides 112 as illustrated in FIG. 20. Additionally, the finger grip 16 may include an elongated deployment element opening 22 having an elongated direction 108 wherein the flattened finger grip sides 112 define first and second planes that are substantially parallel to the elongated direction 108 as illustrated in FIG. 20.

In various embodiments, the finger grip 16 may have a flared end 172 as illustrated in FIGS. 2-4. The flared end 172 may have any suitable angle and may provide additional leverage to remove the pull-activated applicator 10 after expulsion.

The barrel 14 and the finger grip 16 together define the length of the applicator as measured from the insertion end 76 to the finger grip end 78. In contrast, the length of the prior art applicators also included a plunger. The present invention is believed to be more discreet and easier to handle because of the relatively shorter length due to the absence of a traditional plunger. Some prior art applicators used a compact design wherein the plunger was initially reduced in length and then extended prior to use. However, this still resulted in a longer applicator at the time of usage (i.e., after extension of the plunger). For example, prior art applicators typically had lengths at the time of usage greater than 115 mm. In contrast, the present applicators may have an applicator length of less than about 100 mm, less than about 90 mm, or less than about 85 mm. In some embodiments, the present applicators may have a length of about 82 mm.

As discussed above, the internal space 26 of the pull-activated applicator 10 also includes one or more directional transition elements 58. The directional transition elements 58 may be any suitable structure that redirects force applied to the deployment element 18 from a first direction 34 to a second direction 36 wherein the second direction 36 is different than the first direction 34. The directional transition elements 58 are generally located within the internal space 26 and generally include rounded edges to minimize drag as the deployment element 18 moves over the directional transition elements 58 during assembly and deployment.

The directional transition elements 58 may be part of the barrel 14 or the finger grip 16 or combinations thereof. In some embodiments, the directional transition elements 58 may be discrete elements located within the internal space 26.

In some embodiments, the pledget holder 30 may also include one or more directional transition elements 58. Specifically, as illustrated herein, edges of the pledget holder 30 may constitute the directional transition elements 58. In embodiments having two or more directional transition elements 58, the edge of the pledget holder 30 may constitute a first directional transition element 90 positioned opposite a second directional transition element 92 as illustrated in FIG. 12.

The directional transition elements 58 may be located at any suitable longitudinal position along the internal space 26. For example, referring now to FIGS. 21 and 22, the directional transition elements 58 may be located at any suitable distance 146 as measured from the insertion end 76. In various embodiments, the distance 146 may be at least 5 mm, at least 10 mm, at least 15 mm, at least 20, or at least 25 mm. In some embodiments, the distance 146 may be about 35 mm. In some embodiments, the directional transition elements 58 may be located in the internal space 26 proximate the insertion end 76. This positioning may be beneficial when used in conjunction with a barrel 14 having a relatively blunt insertion end 76 and/or embodiments without a pusher 32.

In various embodiments, the directional transition elements 58 may be positioned at a distance 146 of 3 mm to 50 mm from the insertion end 76 of the barrel 14. In some embodiments, the directional transition elements 58 may be positioned at a distance 146 of 25 mm to 40 mm from the insertion end 76 of the barrel 14.

Figure 21:
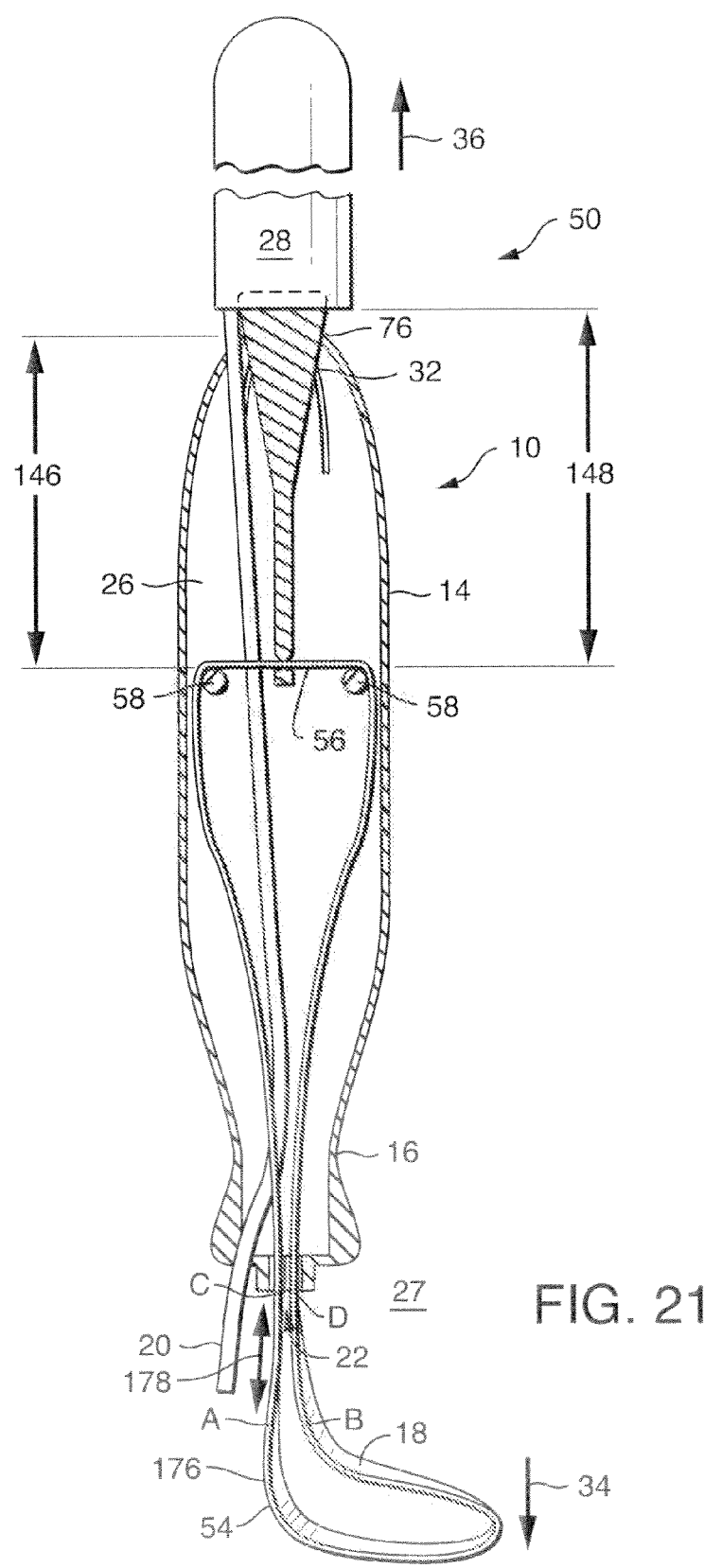
FIG. 21 is a cross-sectional view of an exemplary pull-activated applicator.
Figure 22:
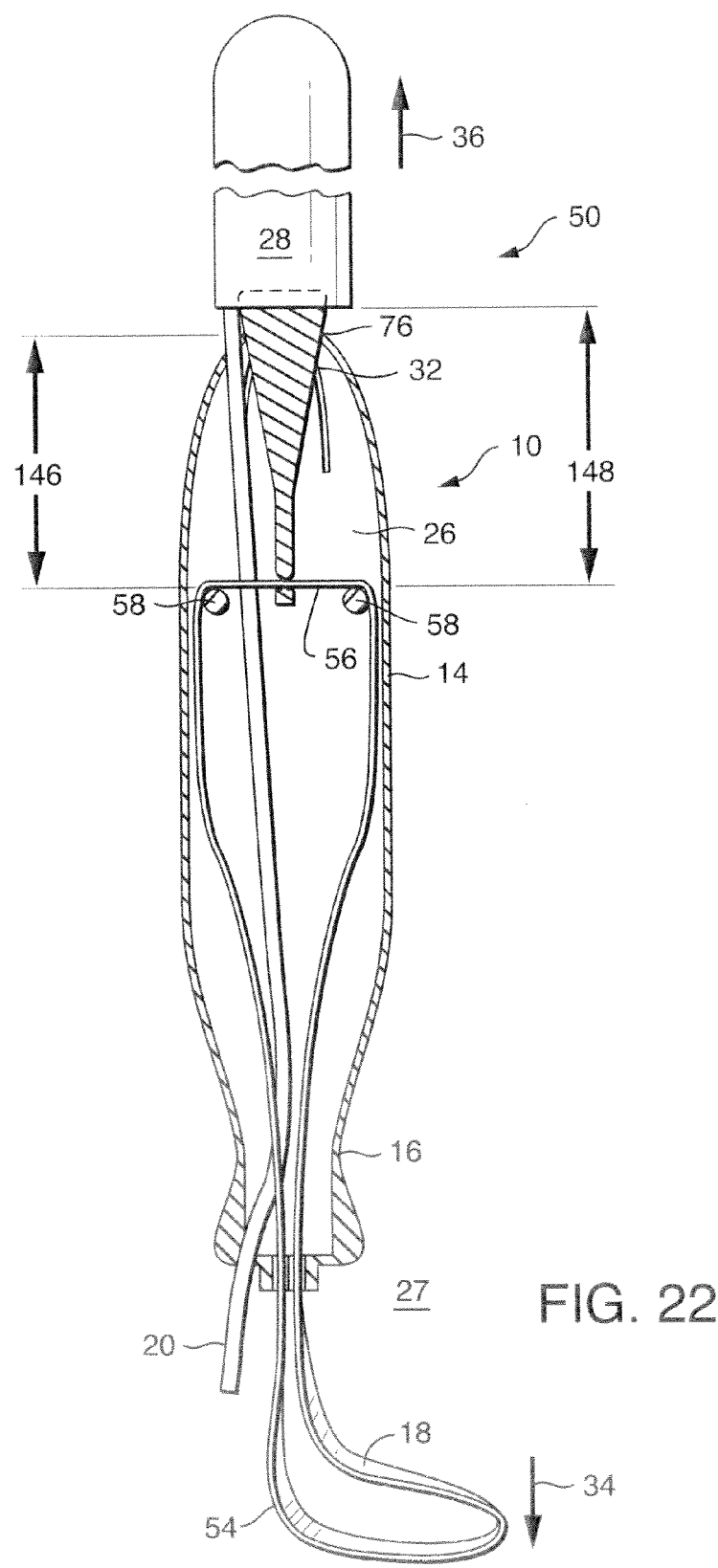
FIG. 22 is a cross-sectional view of an exemplary pull-activated applicator.

As can be seen in FIGS. 21 and 22, the position of the directional transition elements 58 in the internal space 26 defines the upper position of the deployment element 18. In other words, the deployment element 18 does not pass any closer to the insertion end 76 than the distance 146. Thus, if the pledget 28 is to be fully expelled from the barrel 14 and past the insertion end 76, the pusher 32 must have a length 148 in the longitudinal direction equal to or greater than the distance 146. The pusher length 148 is measured from the point the deployment element 18 contacts the pusher 32 to the point the pledget 28 contacts the pusher 32. However, it will be readily appreciated that in some embodiments, the pusher 32 may be sized and/or the directional transition elements 58 positioned such that the pledget 28 is not fully expelled from the barrel 14 after full deployment. Likewise, the directional transition elements 58 may be positioned such that no pusher 32 is utilized and the pledget 28 is not fully expelled from the barrel 14 after full deployment. For example, in some embodiments, at least 5 mm, at least 10 mm, at least 15 mm, or at least 20 mm of the pledget 28 remains in the barrel 14 after full deployment of the applicator.

Referring now to FIG. 21, a cross sectional view of another exemplary pull-activated applicator 10 is illustrated. The pull-activated applicator 10 includes a barrel 14, a finger grip 16, and a deployment element 18. In this embodiment, the barrel 14 and finger grip 16 are representatively illustrated as a unitary structure. The barrel 14 and the finger grip 16 define an internal space 26. The internal space 26 also includes two directional transition elements 58. The directional transition elements 58 are positioned a distance 146 from the insertion end 76 of the pull-activated applicator 10. The deployment element 18 defines a grasping portion 54 and a reserve portion 56. The grasping portion 54 is generally the portion of the deployment element 18 that starts in the external space 27 and is engaged by the user to deploy the pledget 28. The reserve portion 56 is generally that portion of the deployment element 18 that starts in the internal space 26 and extends from the directional transition element 58 to the pusher 32 and back to the directional transition element 58. In use, the deployment element 18 is pulled in the direction 34 until all the reserve portion 56 between the directional transition elements 58 has been taken up. The deployment element 18 in turn causes the pusher 32 to move in the direction 36 and thereby expel the pledget 28.

Referring now to FIG. 22, a cross sectional view of another exemplary pull-activated applicator 10 is illustrated. The pull-activated applicator 10 includes a barrel 14, a finger grip 16, and a deployment element 18 like FIG. 21 but in this embodiment the two directional transition elements 58 are positioned closer to the insertion end 76. As such, the pledget 28 can be fully expelled the same distance as FIG. 21 with a shorter pusher 32.

In various embodiments, the pledget holder 30 provides an internal structure for supporting and aligning the pledget 28. The pledget holder 30 may also be adapted to route the deployment element 18 around the pledget 28. The pledget holder 30 may be made of any suitable material. In some embodiments, the pledget holder 30 may be made of any suitable thermoplastic such as polyester, low density polyethylene, polypropylene, and the like, and combinations thereof. In some embodiments, the pledget holder 30 may be made of foam. In one embodiment, the finger grip 16, the pledget holder 30, and the directional transition element 58 may be made of polypropylene and the barrel 14 may be made of polyethylene. This combination is believed to provide the benefit of both strength in the finger grip 16, the pledget holder 30, and the directional transition element 58 and gentle flexibility in the barrel 14.

Figure 23:
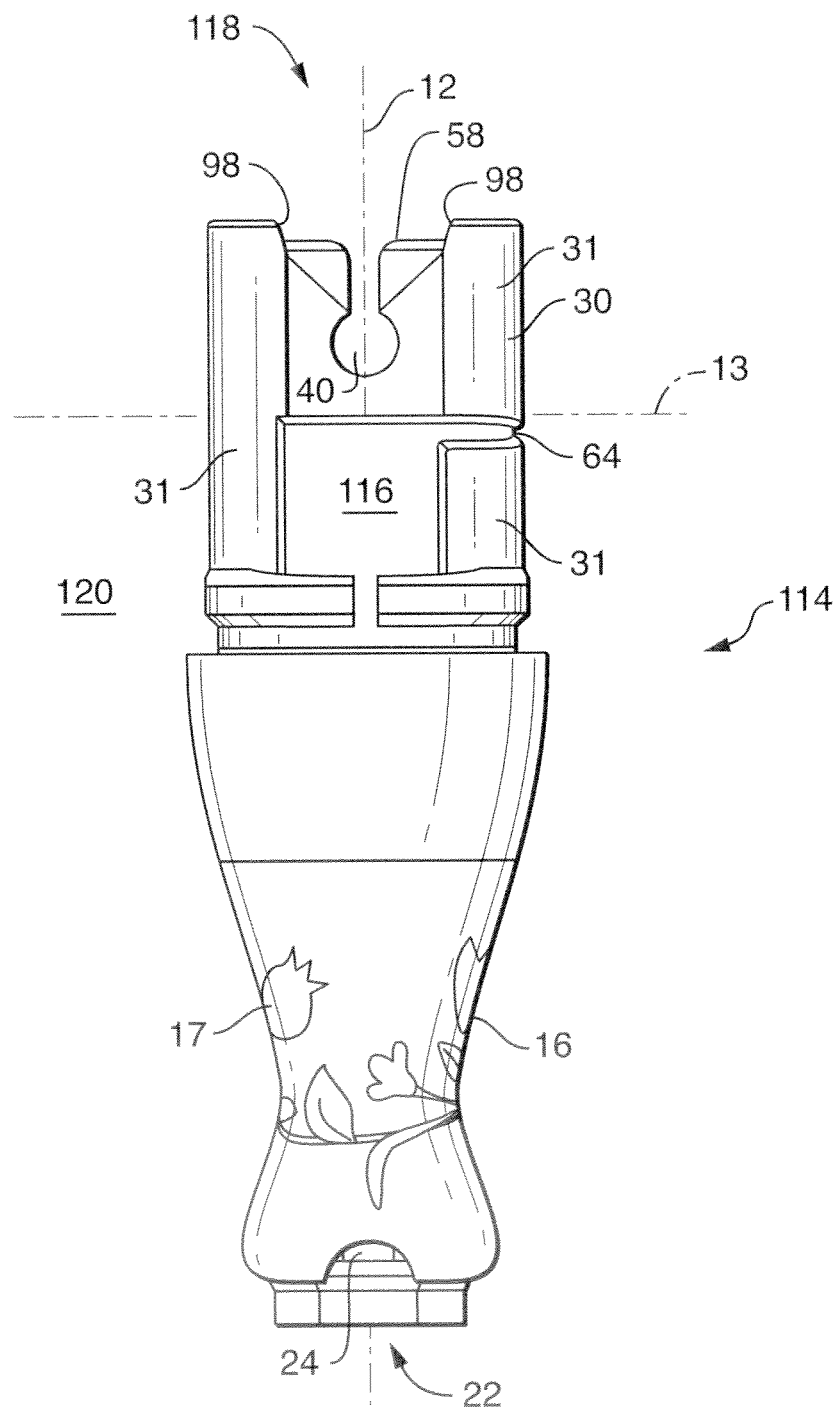
FIG. 23 is a side view of an exemplary pledget holder and finger grip.
Figure 24:
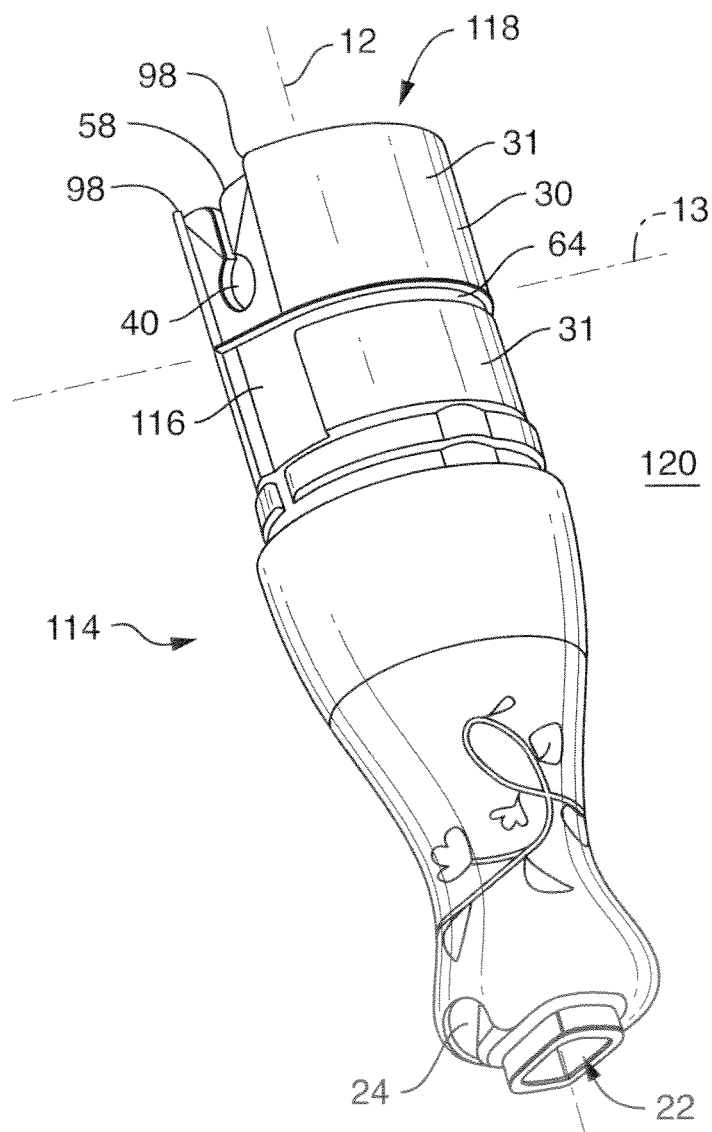
FIG. 24 is a second side view of the pledget holder and finger grip of FIG. 23.

In various embodiments, the finger grip 16 and the pledget holder 30 may be separate pieces or may be a unitary structure. For example, FIG. 23 is a side perspective view of an exemplary pledget holder 30 and finger grip 16 joined together to define a unitary structure 114. FIG. 24 is a second side perspective view (rotated about the longitudinal centerline 12) of the exemplary unitary structure 114 of FIG. 23.

Referring now, to FIGS. 23 and 24, a pledget holder 30 and a finger grip 16 may be joined together by any suitable means to define a unitary structure 114. For example, the pledget holder 30 and the finger grip 16 may be formed as a single piece. Alternatively, the pledget holder 30 and the finger grip 16 may be formed independently and joined together mechanically, thermally, adhesively, or the like, or combinations thereof. In other embodiments, the pledget holder 30 and the finger grip 16 may be formed independently and positioned in relative proximity to each other but not joined to each other.

In various embodiments, the pledget holder 30 may include a key hole 40. In some embodiments, the pledget holder 30 may include one or more directional transition elements 58 as illustrated in FIGS. 23 and 24. In some embodiments, the pledget holder 30 includes a first directional transition element 90 and a second directional transition element 92 as illustrated in FIG. 12. In FIGS. 23 and 24 only one of the directional transition elements 58 is visible.

Figure 31:
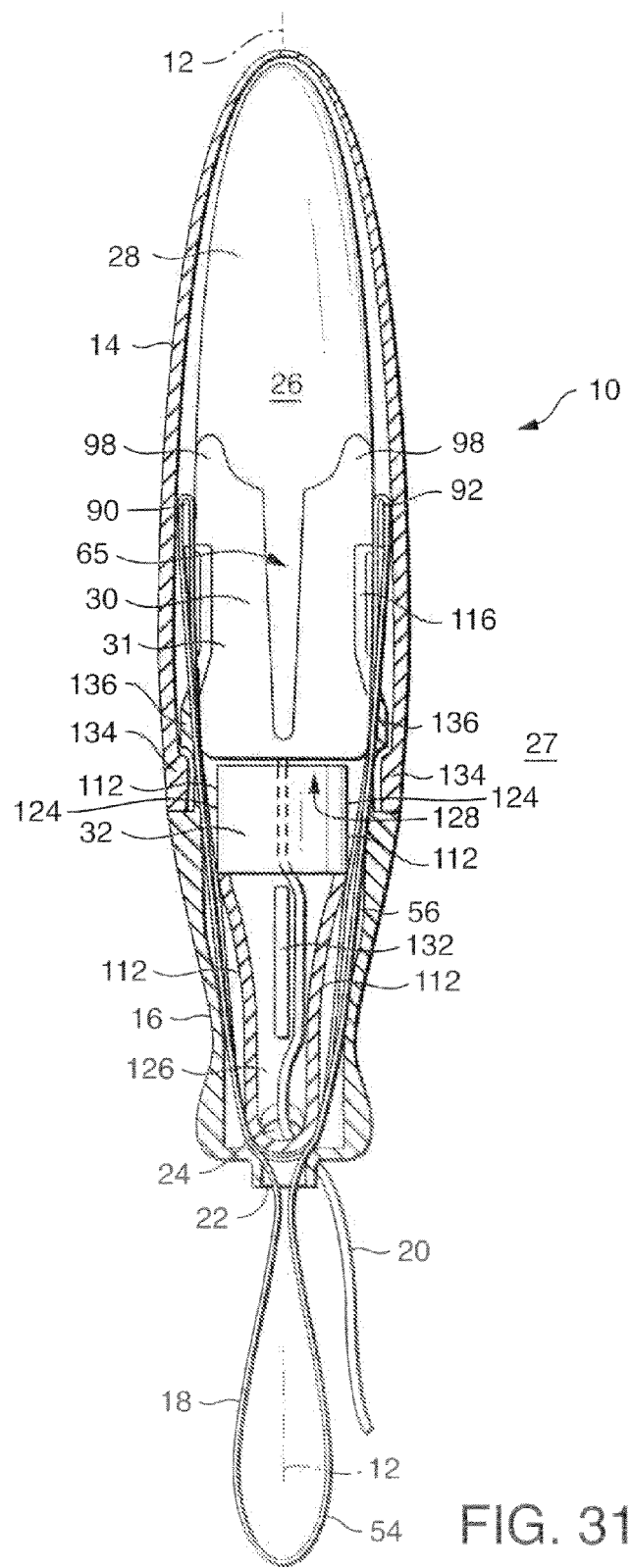
FIG. 31 is a side view of an exemplary pull-activated applicator with portions cut away to illustrate internal components and structure.

In some embodiments, the directional transition elements 58 may be flanked by one or more tracking guides 98. The tracking guides 98 facilitate initial alignment of the deployment element relative to the directional transition elements 58 during assembly. Additionally, the tracking guides 98 facilitate alignment of the deployment element 18 during use, as illustrated in FIG. 31. In some embodiments, the tracking guides 98 may also serve as a "pilot" to assist in aligning the pledget holder 30 with the barrel 14 during assembly. In other words, the tracking guides 98 may provide a point of early contact between the pledget holder 30 and the barrel 14 to facilitate insertion of the pledget holder 30 into the barrel 14.

Figure 27:
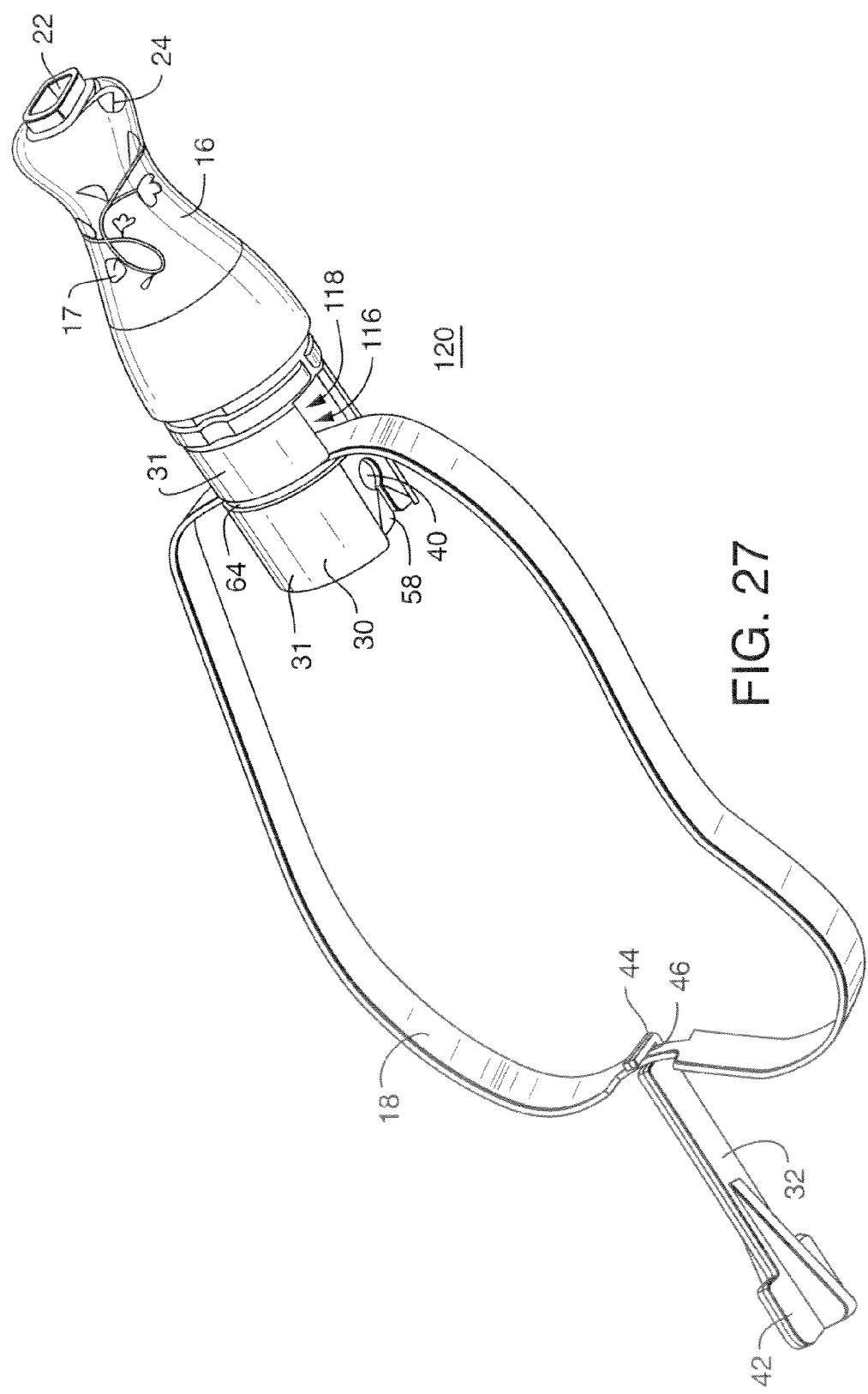
FIG. 27 is a perspective view of an exemplary pusher and deployment element assembly engaged with an exemplary pledget holder.
Figure 38:
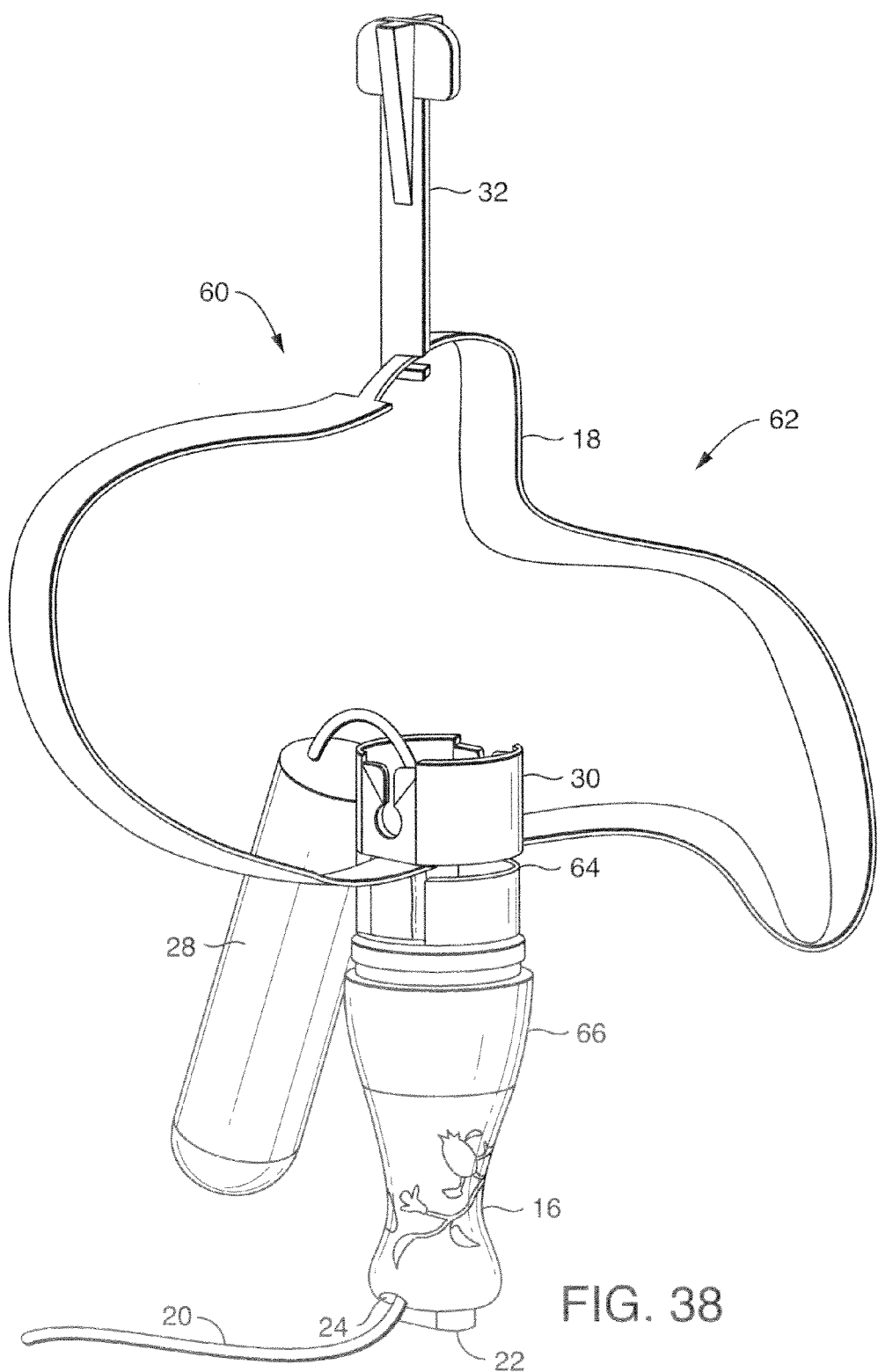

In some embodiments, the pledget holder 30 may include a first slot 64. As illustrated in FIGS. 23 and 24, the first slot 64 may be oriented in a direction 13 that is generally perpendicular to the longitudinal centerline 12. The first slot 64 facilitates assembly of the deployment element 18 with the pledget holder 30. Specifically, the first slot 64 allows the deployment element 18 to be threaded through the pledget holder wall 30 to access the deployment element passage 116 as illustrated in FIG. 27. This configuration is particularly beneficial for assembly when the deployment element 18 is joined as a loop prior to integration with the pledget holder 30 as illustrated in FIGS. 27 and 38. In use, the deployment element 18 and the pledget holder 30 are adapted such that first slot 64 closes during expulsion of the pledget 28 due to the downward forces applied to the directional transition elements 58. This closure of the first slot 64 minimizes the possibility of the deployment element 18 escaping through the first slot 64 during expulsion of the pledget 28.

Figure 39:
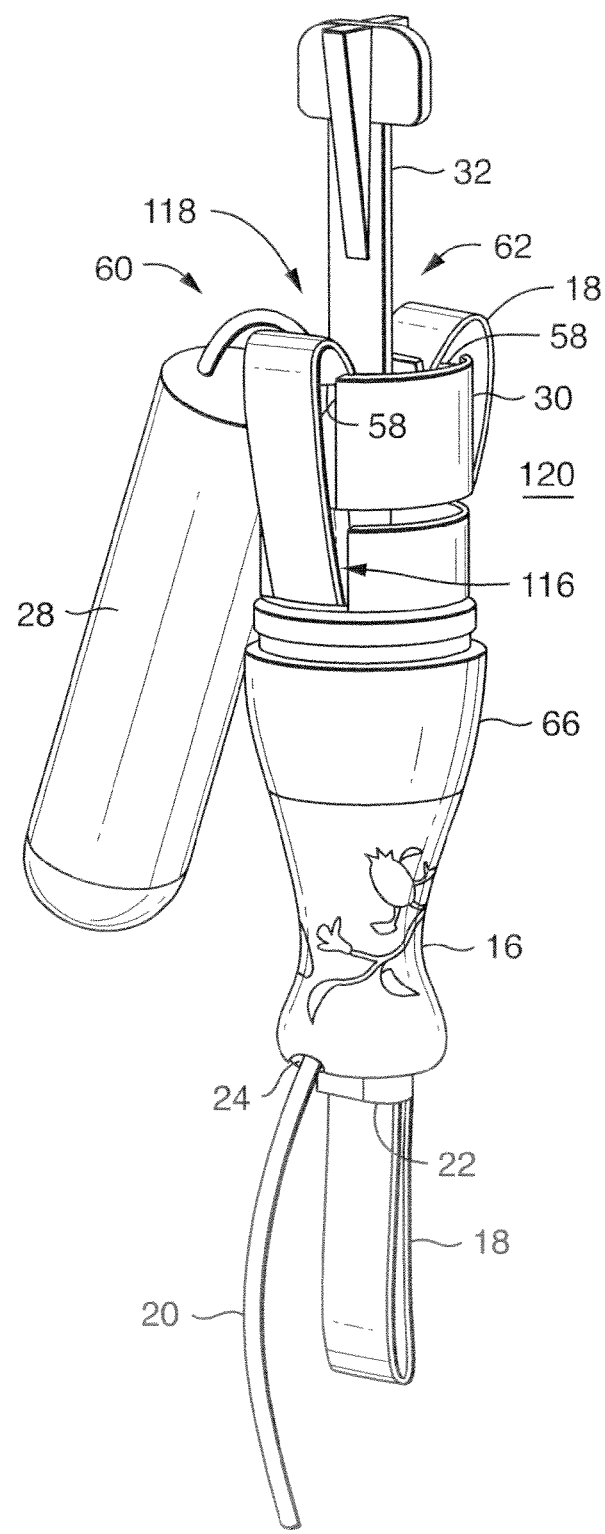

In some embodiments, the pledget holder 30 may include a deployment element passage 116 as representatively illustrated in FIGS. 23-27. The deployment element passage 116 allows the deployment element 18 to move between a pledget holder internal space 118 and a pledget holder external space 120. In use, and as illustrated in FIG. 39, the deployment element 18 passes from the internal space 118 through the deployment element passage 116 to the external space 120. From the external space 120, the deployment element 18 moves over a directional transition element 58 and back into the internal space 118. Once in the internal space, the deployment element 18 passes under a pledget 28 back into the external space 120 and over another directional transition element 58. Finally, the deployment element passes from the external space 120 through the deployment element passage 116 to the internal space 118.

Figure 25:
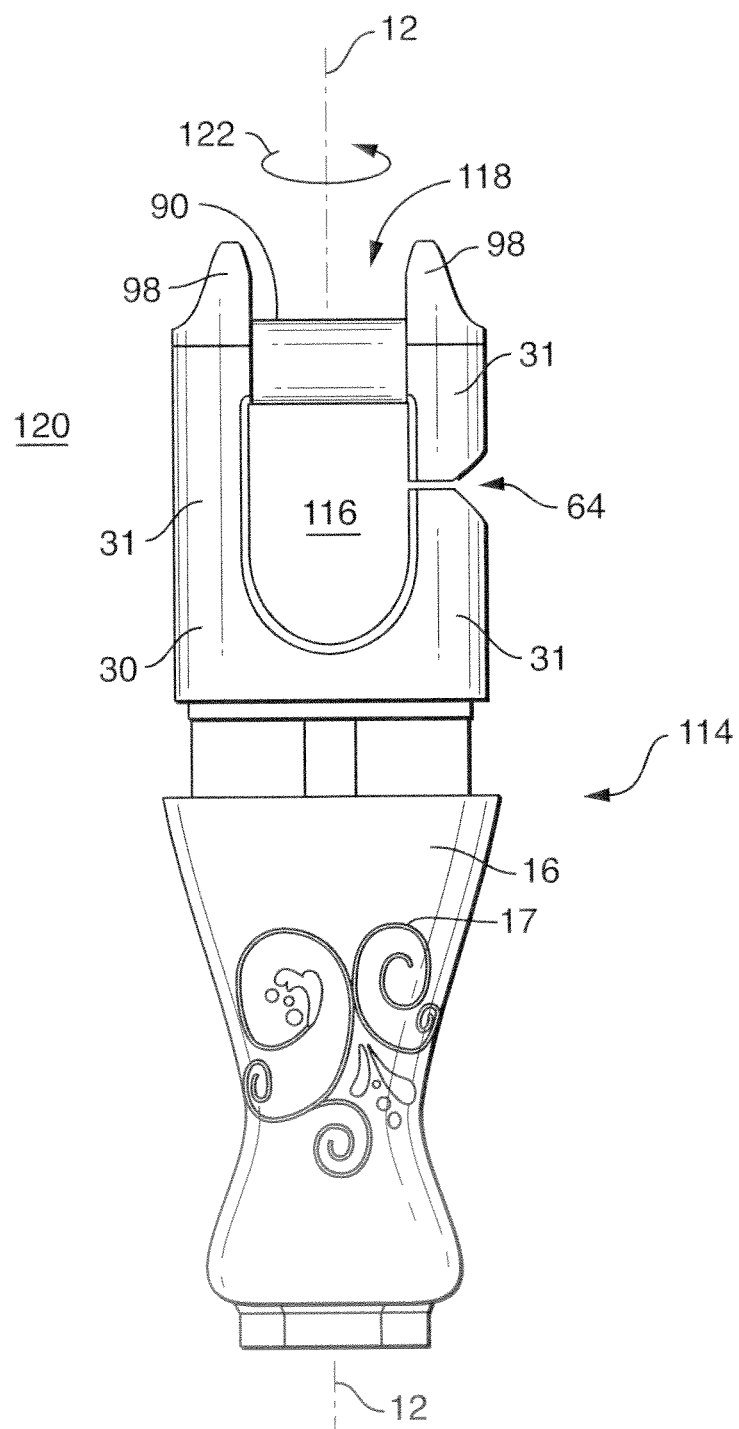
FIG. 25 is a side view of an exemplary pledget holder and finger grip.
Figure 26:
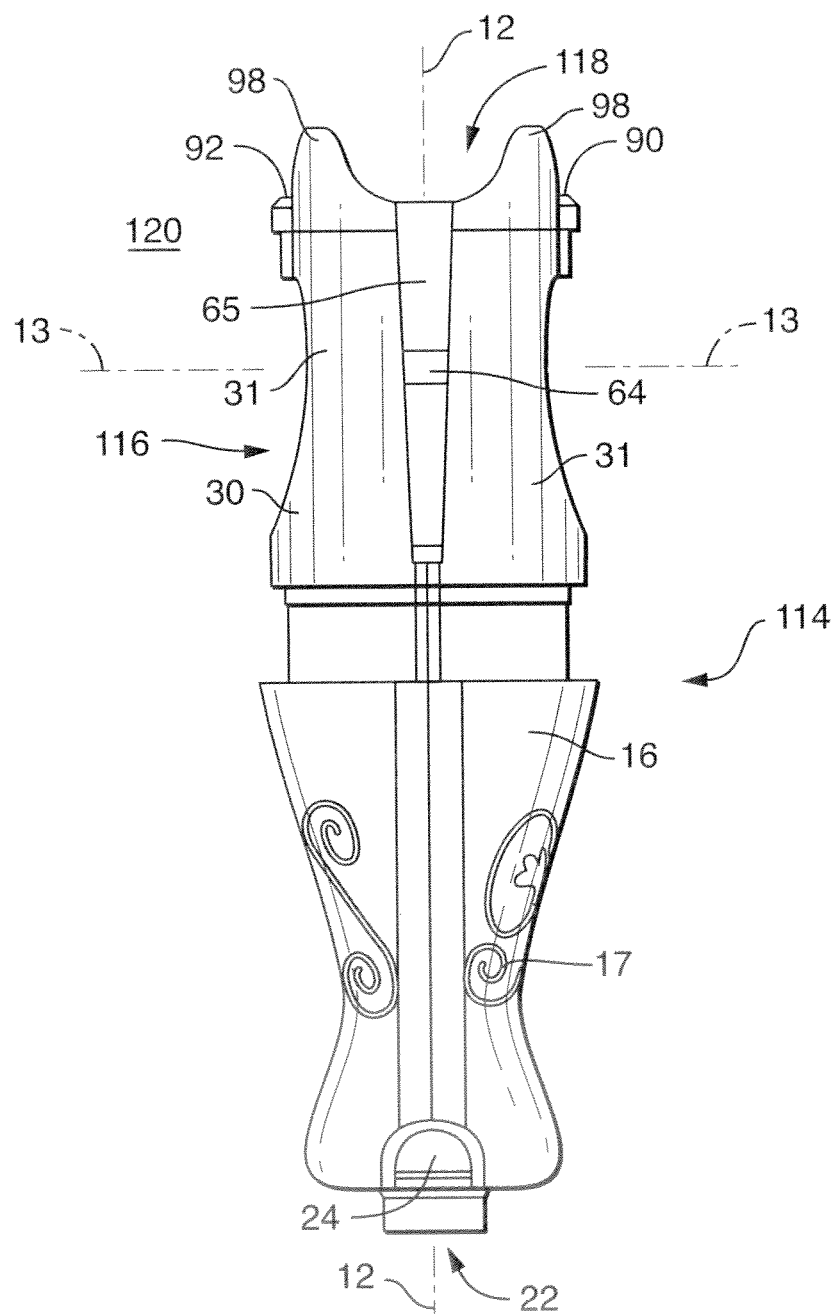
FIG. 26 is a second side view of the pledget holder and finger grip of FIG. 25.

In another example, FIGS. 25 and 26 representatively illustrate another exemplary pledget holder 30. Specifically, FIG. 25 is a side perspective view of pledget holder 30 and finger grip 16 joined together to define a unitary structure 114. FIG. 26 is second side perspective view of the exemplary unitary structure 114 of FIG. 25 rotated in the direction 122 about the longitudinal centerline 12.

The pledget holder 30 and the finger grip 16 of FIGS. 25 and 26 are illustrated as a unitary structure 114 and may be formed as a single piece or may be formed independently and joined together mechanically, thermally, adhesively, or the like, or combinations thereof. Alternatively, the pledget holder 30 and the finger grip 16 of FIGS. 25 and 26 may be formed independently and positioned in relative proximity to each other but not joined to each other.

The pledget holder 30 includes a first directional transition element 90 and a second directional transition element 92. The first directional transition element 90 and the second directional transition element 92 are flanked by tracking guides 98. The tracking guides 98 facilitate initial alignment and alignment of the deployment element 18 relative to the directional transition elements 90 and 92 during use.

In some embodiments, the pledget holder 30 may include a first slot 64 and a second slot 65. For example, as illustrated in FIG. 26, the first slot 64 may be oriented in a direction 13 that is generally perpendicular to the longitudinal centerline 12. The first slot 64 facilitates assembly of the deployment element 18 with the pledget holder 30. Specifically, the first slot 64 allows the deployment element 18 to be threaded through the pledget holder wall 31 to access the deployment element passage 116 as illustrated in FIG. 27. The deployment element passage 116 allows the deployment element 18 to move between a pledget holder internal space 118 and a pledget holder external space 120 as described above.

The second slot 65 may be oriented in a direction that is generally parallel to the longitudinal centerline 12. The second slot 65 facilitates assembly of the pledget holder 30 within the barrel 14. Specifically, the second slot 65 allows the pledget holder walls 31 to have a greater degree of freedom to flex past any narrow portions (e.g., seaming beads or collars) during assembly. Once the pledget holder 30 passes any narrow portions of the barrel 14, the pledget holder walls 31 return to the initial position.

The pusher 32 may be made of any suitable material. In some embodiments, the pusher 32 may be made of any suitable thermoplastic such as polyester, low density polyethylene, polypropylene, and the like, and combinations thereof. In some embodiments, the pusher 32 and the deployment element 18 may be made of compatible materials to facilitate joining of the two elements. For example, in some embodiments, the pusher 32 and the deployment element 18 may be made from the same polymer resin. In some embodiments, the polymer resin may be a polyester material. For example, the polyester material may have an intrinsic viscosity of about 0.75 dL/g, a moisture content of about 0.25% by weight, and a melting temperature of about 250-280 degrees C.

In various embodiments, the pusher 32 may be any suitable shape and size. The pusher 32 provides a positive point of contact between the deployment element 18 and the pledget 28. The pusher 32 allows the pledget 28 to be expelled past the directional transition elements 58, 90, and 92 by a distance equal to the length 148 of the pusher 32 as illustrated in FIGS. 21 and 22. In various embodiments, the length 148 of the pusher 32 may be about 1 mm to about 65 mm in length. In some embodiments, the length 148 of the pusher 32 may be about 20 mm to 40 mm in length. In some embodiments, the length 148 of the pusher 32 may be about 30 mm.

In various embodiments, the pusher 32 may have a shape that facilitates the deployment element 18 and/or the withdrawal string 20 passing along the sides of the pusher 32. Additionally, the pusher 32 may have a shape that works in coordination with the shape of the finger grip 16 to minimize or prevent rotation of the pusher 32 within the finger grip 16.

Figure 28:
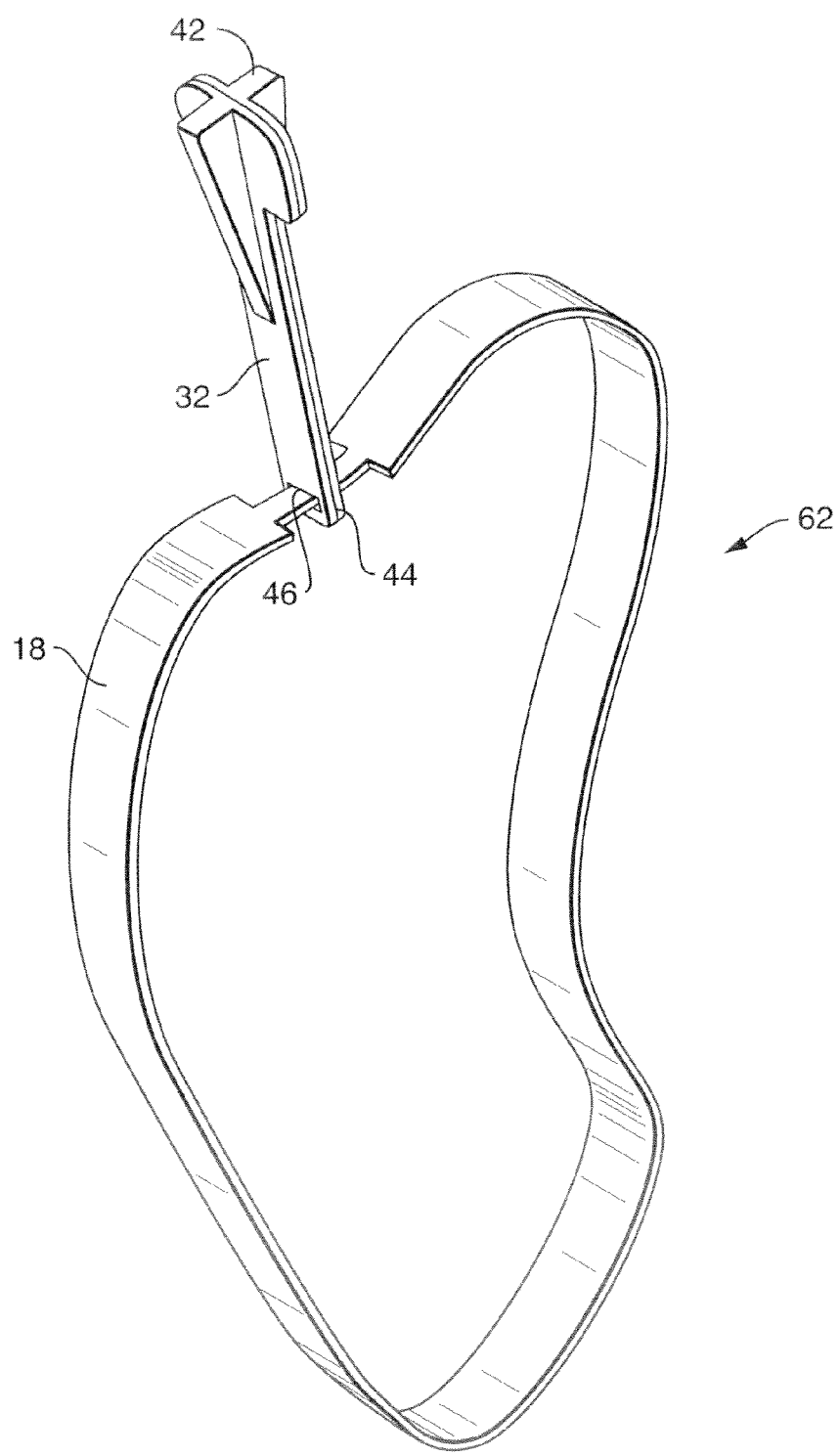
FIG. 28 is a perspective view of an exemplary pusher and deployment element assembly.

Referring now to FIG. 28, an exemplary pusher 32 is illustrated. FIG. 28 is a perspective view of an exemplary pusher 32 joined with an exemplary deployment element 18 to form a deployment pre-assembly 62. The pusher 32 has a pledget end 42 and a deployment element end 44. In use, the pledget end 42 is oriented towards the pledget 28 and pushes the pledget 28 from the internal space 26 of the barrel 14 when force is applied to the deployment element 18. In some embodiments, the pledget end 42 may also extend into the pledge 28 to control the orientation of the pledget 28 within the vaginal canal.

Figures 29, 30:
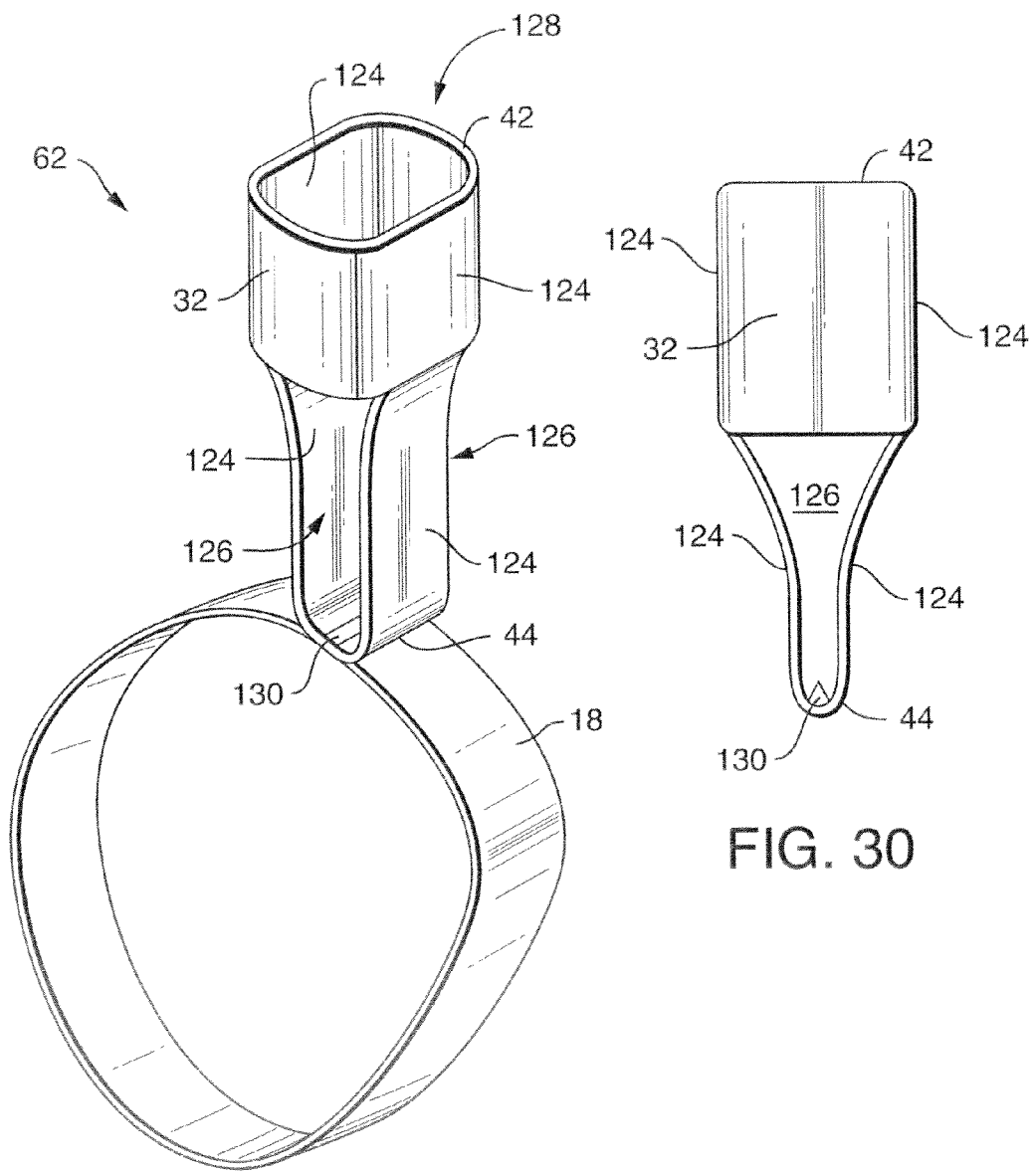
FIG. 29 is a perspective view of an exemplary pusher and deployment element assembly.
FIG. 30 is a side view of the pusher of FIG. 29.

Referring now to FIGS. 29 and 30, another exemplary pusher 32 is illustrated. FIG. 29 is a perspective view of the pusher 32 joined with a deployment element 18 to form a deployment pre-assembly 62. FIG. 30 is a side view of the pusher 32 of FIG. 29. The pusher 32 has a pledget end 42 and a deployment end 44. Once assembled, the pledget end 42 is oriented towards the pledget 28 and the deployment element end 44 is in contact with and may be joined to the deployment element 18. The pusher 32 of FIGS. 29 and 30 includes flattened pusher sides 124, pusher side openings 126, energy director 130, and a pledget end opening 128.

The pusher side openings 126 and the pledget end opening 128 are included in various embodiments to allow the withdrawal string 20 to pass through the pusher 32. Additionally, the pusher side openings 126 and the pledget end opening 128 reduce the amount of materials necessary for construction of the pusher 32 and facilitate assembly by allowing increased airflow past and through the pusher 32. This is particularly beneficial when vacuum is used to direct the withdrawal string 20 through a portion of the pusher 32 and out the withdrawal string opening 24. Thus, in some embodiments, the withdrawal string 20 is attached to the pledget 28, passes through the pledget end opening 128 of the pusher 32, passes out of the pusher 32 through one of the pusher side openings 126, and exits the finger grip 16 via the withdrawal string opening 24 as illustrated in FIG. 31.

Referring now to FIG. 31, an assembled pull-activated applicator 10 is illustrated with portions cut away to illustrate internal features. Specifically, the barrel 14 is shown in cross section to illustrate the pledget 28, pledget holder 30, directional transition elements 90 and 92, and deployment element 18 located therein. Likewise, the finger grip 16 is shown in cross section to illustrate the pusher 32, an anti-rotation fin 132, the deployment element 18, the withdrawal string 20, and the withdrawal string opening 24 located therein.

In various embodiments, the flattened pusher sides 124 may be configured to provide additional space between the pusher 32 and the finger grip 16 to facilitate the deployment element 18 passing between the pusher 32 and the finger grip 16 when the pull-activated applicator is fully assembled as illustrated in FIG. 31. The flattened pusher sides 124 also facilitate the deployment element 18 passing between the pusher 32 and the pledget holder 30 during deployment.

In various embodiments, the pusher 32 may include an energy director 130 to facilitate joining the pusher 32 with the deployment element 18. The energy director 130 may include an additional mass of material located at the point the pusher 32 is joined with the deployment element 18 as illustrated in FIGS. 29 and 30. The use of one or more energy directors 130 is particularly beneficial when the deployment element 18 and the pusher 32 are joined by ultrasonic bonding. During the ultrasonic bonding operation, energy is focused at the energy director 130 which softens and bonds to the deployment element 18. The additional material associated with the energy director 130 allows for some material to flow at the bond point without weakening or cutting the pusher 32.

In some embodiments, the pusher 32 may work in cooperation with one or more anti-rotation fins 132 to minimize or prevent the pusher 32 from rotating within the finger grip 16. For example, an anti-rotation fin 132 may be attached to the inner surface of the finger grip 16 as illustrated in FIG. 31. The anti-rotation fin 132 may extend from the surface of the finger grip 16 any suitable distance such that anti-rotation fin 132 does not interfere with the operation of the pusher 32 but prevents the pusher 32 from rotating. In some embodiments, one or more anti-rotation fins 132 may be joined to the inner surface of the finger grip 16 and extend into the space created by the flattened pusher sides 124. In these embodiments, the pusher 32 may rotate until one of the flattened pusher sides 124 contacts an anti-rotation fin 132.

The deployment element 18 may be made of any suitable material using any suitable process. For example, the deployment element 18 may include thermoplastic films, extrusions, castings, molds, and the like. In some embodiments, the deployment element 18 may include woven and nonwoven fabrics, stranded or braided materials, or the like, or combinations thereof. Suitable thermoplastics include polyester, low density polyethylene, polypropylene, thermoplastic elastomers, and the like, and combinations thereof. In some embodiments, the deployment element 18 may be a non-extensible woven ribbon that is made of a thermoplastic material like polyester, low density polyethylene, or the like, or combinations thereof. In various embodiments, the deployment element 18 may have a single-sided or double-sided satin weave. In a specific embodiment, the deployment element 18 may include multiple yarn threads in the warp direction. Each yarn thread may include 36 polyester filaments to achieve a denier of about 70. Additionally, the yarn threads may be included such that there are about 320 warp ends per inch. In some embodiments, the deployment element 18 may also include a single polyester monofilament having a denier of about 30 in a weft direction and about 48 threads (picks) per inch.

In various embodiments, the deployment element 18 may have embossed edges or may have thermally slit edges. In some embodiments, the deployment element 18 may include a satin weave and may have tubular woven edges. While not wishing to be bound by theory, it is believed that embossed edges and/or tubular woven edges minimize fraying when used with various materials. For example, when using a woven polyester, embossing the edges or using a tubular weave on the edges is believed to minimize fraying.

In various embodiments, the deployment element 18 may be sized to promote one handed operation. Specifically, the deployment element 18 may be presented in a loop configuration such that the user may grasp the finger grip 16 with the thumb and middle finger and engage the deployment element 18 with the index finger. In specific embodiments, the deployment element 18 may have a total length of 200 mm to 325 mm, 250 mm to 300 mm, or about 270 mm. The total length of the deployment element 18 may be determined by cutting the deployment element 18 perpendicularly to the long direction, removing the deployment element 18 from the interior space 26, laying the deployment element 18 straight, and measuring the deployment element 18 from end to end.

In some embodiments, the deployment element 18 may have a starting loop size 174 as illustrated in FIG. 12. As used herein, the term "starting loop size" means the size of the loop before force is applied to the deployment element 18. The starting loop size 174 is determined by measuring the length of the deployment element 18 from point A to point B. Point A is a first location on the deployment element 18 immediately proximate the deployment element opening 22 before force is applied to the deployment element 18. Point B is a second location on the deployment element 18 immediately proximate the deployment element opening 22 before force is applied to the deployment element 18. In various embodiments, the starting loop size 174 may be 26-90 mm. In other embodiments, the deployment element 18 may have a starting loop size 174 of 50-64 mm. In some embodiments, the deployment element 18 may have a starting loop size 174 of about 56 mm.

In some embodiments, the deployment element 18 may have a finished loop size 176 as illustrated in FIG. 21. As used herein, the term "finished loop size" means the size of the loop after force is applied to the deployment element 18 and after the pledget 28 has been deployed to the maximum extent possible. The finished loop size 176 is determined by measuring the length of the deployment element 18 from point C to point D. Point C is a first location on the deployment element 18 immediately proximate the deployment element opening 22 after maximum deployment of the pledget 28. Point D is a second location on the deployment element 18 immediately proximate the deployment element opening 22 after maximum deployment of the pledget 28. In various embodiments, the finished loop size 176 may be about 100-184 mm, 144-158 mm, or about 150 mm. The starting loop size 174 and the finished loop size 176 are selected to ensure that most users are able to fully deploy the pledget 28 with a single movement of the hand. If the deployment element 18 is too long, the user will have completely extended their finger but will not have completely deployed the pledget 28.

In various embodiments, the deployment element 18 may have a stroke length 178 as illustrated in FIG. 21. The stroke length 178 is the distance from point A to point C or the distance from point B to point D. In some embodiments, the deployment element 18 may have a stroke length 178 of about 30-50 mm, about 40 to 50 mm, or about 47 mm.

In various embodiments, the deployment element 18 may have any suitable width 150 as illustrated in FIG. 1. In some embodiments, the width 150 may be at least 3 mm, at least 4 mm, or at least 5 mm. In some embodiments, the width 150 may be about 6 mm. In various embodiments, the deployment element 18 may have any suitable thickness 152 as illustrated in FIG. 2. In some embodiments, the thickness 152 may be less than 2 mm, less than 1 mm, or less than 0.5 mm. In some embodiments, the thickness 152 may be about 0.10 to about 0.20 mm or about 0.16 mm. In some embodiments, the ratio of the deployment element width 150 to the deployment element thickness 152 may be greater than 5, greater than 10, greater than 15, greater than 20, greater than 25, greater than 30, greater than 35, greater than 40, or greater than 45. In some embodiments, the ratio of the deployment element width 150 to the deployment element thickness 152 may be about 40-60.

While not wishing to be bound by theory, it is believed that deployment elements having greater widths will be less likely to "roll" on the user's finger during deployment. Likewise, it is believed that deployment elements having a ratio of width to thickness of greater than 2 will also be less likely to "roll" during deployment.

In various embodiments, the deployment element 18 may have different widths 150 and/or different thicknesses 152 at different points along the deployment element 18. For example, the deployment element 18 may have a first width 154 in the internal space 26 and a second width 156 in the external space 27. In various embodiments, the first width 154 may be greater than, equal to, or less than the second width 156. Thus, in some embodiments, portions of the deployment element 18 in the internal space 26 may have a first width 154 that is smaller than portions of the deployment element 18 having a second width 156 in the external space 27 as illustrated in FIG. 7. The difference in widths may accommodate various deployment cues and/or may accommodate customization of the deployment element 18 at various points. For example, it may be desirable in some embodiments to utilize a deployment element 18 having a narrower width 154 in the internal space 26 to allow greater freedom of movement during loading and deployment. A narrower width 154 may also be advantageous to reduce material costs. Likewise, it may be desirable in some embodiments to utilize a deployment element 18 having a wider width 156 in the external space 27 to provide the user with greater control, more comfort, and/or more visual appeal with the grasping portion 54 of the deployment element 18.

In various embodiments, the deployment element 18 may have any suitable bending stiffness as measured using a Kawabata Evaluation System (KES) Pure Bend Electronic Unit KES-FB-2 and a KES Pure Bend Mechanical Unit. In some embodiments, the deployment element 18 may have a bending stiffness of about 0.4 to about 0.6 or about 0.54 grams-force*cm$^2$/cm. In comparison, a standard removal string has a bending stiffness of about 0.014 grams-force*cm$^2$/cm.

In some embodiments, the deployment element 18 may include more than one material. For example, in some embodiments, a portion of the deployment element 18 in the internal space 26 may be made of a first material whereas a portion of the deployment element 18 in the external space 27 may be made of a second material. In various embodiments, the first material and the second material may be the same or may be different. The deployment element 18 having two different materials may provide for greater customization of the deployment element 18 to accommodate different needs. For example, the deployment element 18 may have a first material that is optimized for use in the internal space 26 of the pull-activated applicator 10. In contrast, the same deployment element 18 may have a second material that is optimized for use in the external space 27 of the pull-activated applicator 10. In some embodiments, the first material may have different material properties than the second material. For example, the first material may be stronger, narrower, slicker, and/or less aesthetically pleasing whereas the second material may be softer, wider, and/or more aesthetically pleasing. The two or more different materials used for the deployment element 18 may be any suitable material, including those discussed herein. Likewise, the two or more different materials used for the deployment element 18 may be joined together using any suitable means such as thermal bonding, ultrasonically bonding, mechanically bonding, adhesively bonding, and the like, and combinations thereof.

In various embodiments, the pledget 28 may be absorbent or non-absorbent. In some embodiments, the pledget 28 may include at least one layer of any suitable absorbent material or combination of absorbent materials. For example, the pledget 28 may be a radially wound absorbent tampon made of viscose and formed into an elongated tubular shape. In some embodiments, the pledget 28 may also include a cover material made of any suitable material. For example, the cover material may include polyester/polyethylene bicomponent fibers.

The pledget 28 may also include a withdrawal string 20 made of any suitable material. For example, the withdrawal string 20 may be made of cotton, rayon, polyester, viscose, or the like, or combinations thereof. In some embodiments, the withdrawal string 20 may be a combination of polyester and viscose. The withdrawal string 20 may include any suitable treatment such as, for example, an anti-wicking agent.

In some embodiments, the pledget 28 may be adapted to accommodate direct contact with the deployment element 18. In other words, in some embodiments, the deployment element 18 may provide deployment force to the pledget 28 directly without use of a pusher 32. In these embodiments, the pledget 28 may be unaltered or may include one or more deformations on the surface in contact with the deployment element 18. For example, the surface of the pledget 28 in contact with the deployment element 18 may include a channel sized and positioned to receive the deployment element 18 therein.

In various embodiments, the pledget 28 may have any suitable cross-sectional shape. For example, the pledget 28 may have a generally circular, rectangular, oval, elliptical, triangular, irregular, or the like cross-sectional shape. Likewise, the barrel 14 may have any suitable cross-sectional shape. For example, the barrel 14 may have a generally circular, rectangular, oval, elliptical, triangular, irregular, or the like cross-sectional shape.

In some embodiments, the cross-sectional shape of the pledget 28 and the cross-sectional shape of the barrel 14 may be selected to provide gaps between the pledget 28 and the barrel 14. For example, in some embodiments, the pledget 28 may have an elliptical cross-sectional shape while the barrel 14 has a circular cross-sectional shape. Likewise, in some embodiments, the pledget 28 may have a circular cross-sectional shape while the barrel 14 has a circular cross-sectional shape.

In various embodiments, the pledget 28 may be any suitable vaginally inserted device. For example, the pledget 28 may be a menstrual tampon, a menstrual cup, a vaginal suppository, a contraceptive device, or a vaginally inserted incontinence device as are known in the art. Exemplary menstrual tampons are taught in U.S. Pat. No. 2,330,257 to Bailey. Exemplary menstrual cups are taught in U.S. Pat. No. 1,891,761 to Goddard. Exemplary vaginal suppositories are taught in U.S. Pat. No. 5,863,553 to Britton. Exemplary contraceptive devices are taught in U.S. Pat. No. 4,360,013 to Barrows. Exemplary vaginally inserted incontinence devices are taught in U.S. Pat. No. 6,142,928 to Zunker.

Suitable menstrual tampons may include "cup" shaped pledgets like those disclosed in U.S. publication 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" type pledgets like those disclosed in U.S. Pat. No. 2,464,310 to Harwood; "M-folded" tampon pledgets like those disclosed in U.S. Pat. No. 6,039,716 to Jessup; or a "bag" type or "unstablized" type tampon pledgets like those disclosed in U.S. Pat. No. 3,815,601 to Schaefer.

In various embodiments, the tampon pledgets may also include one or more additional features. For example, the tampon pledgets may include a "protection" feature as exemplified by U.S. Pat. No. 6,840,927 to Hasse, U.S. publication 2004/0019317 to Takagi, U.S. Pat. No. 2,123,750 to Schulz, and the like. In some embodiments the tampon pledgets may include an "anatomical" shape as exemplified by U.S. Pat. No. 5,370,633 to Villalta, an "expansion" feature as exemplified by U.S. Pat. No. 7,387,622 to Pauley, an "acquisition" feature as exemplified by U.S. publication 2005/0256484 to Chase, an "insertion" feature as exemplified by U.S. Pat. No. 2,112,021 to Harris, a "placement" feature as exemplified by U.S. Pat. No. 3,037,506 to Penksa, or a "removal" feature as exemplified by U.S. Pat. No. 6,142,984 to Brown.

Figure 32:
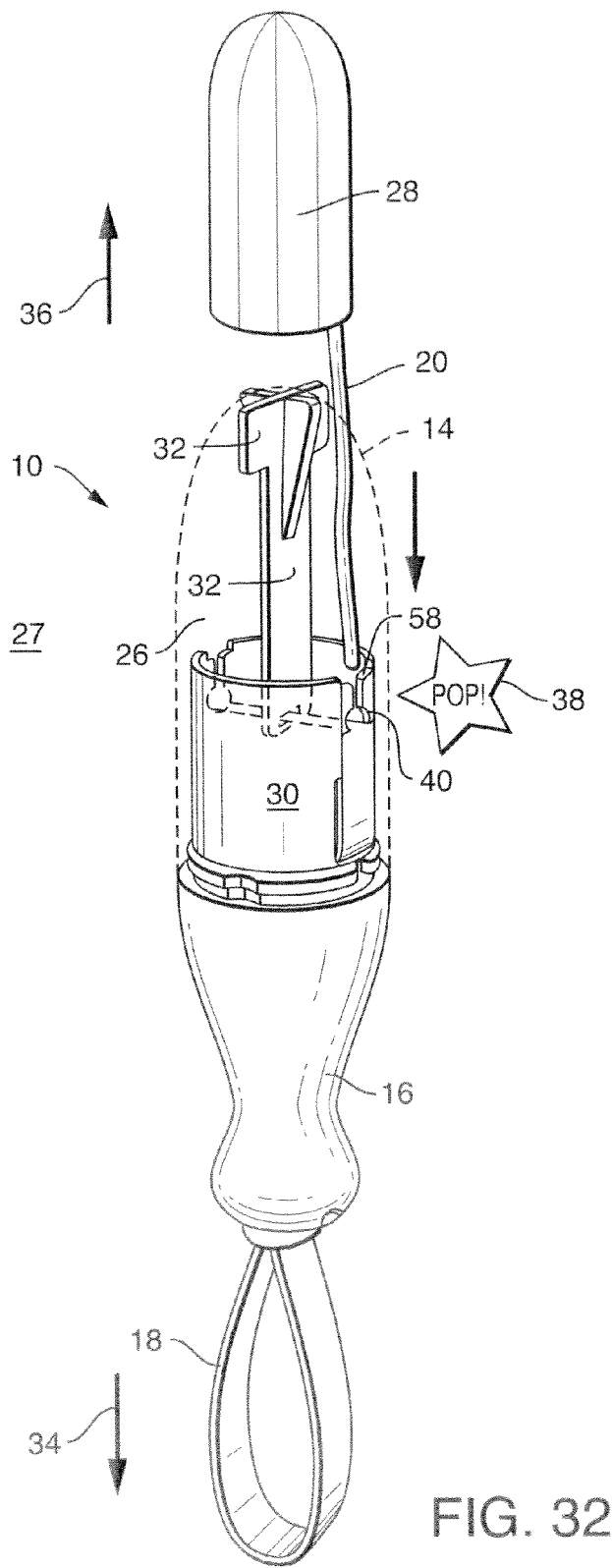
FIG. 32 is a side perspective view of an exemplary pull-activated applicator with portions shown in phantom to illustrate internal structure and an expelled tampon pledget.

In some embodiments, the pull-activated applicator 10 may include a deployment cue 38. For example, FIG. 32 is a side perspective view of an exemplary pull-activated applicator 10 with a pledget 28 expelled from the barrel 14 and a deployment cue 38. In the illustrated embodiment, the deployment cue 38 is an auditory cue such as a "pop" sound and tactile cue such as a noticeable change in pull resistance generated by the deployment element 18 moving into a keyhole 40 in the pledget holder 30. These cues can be enhanced by proper choice of shape, texture, material mechanical properties, size of the deployment element 18 and shape, texture, material mechanical properties, and size of the pledget holder 30 and the keyhole 40. In various embodiments, the deployment cue 38 may be tactile, auditory, olfactory, visual, or combinations thereof.

Figure 33:
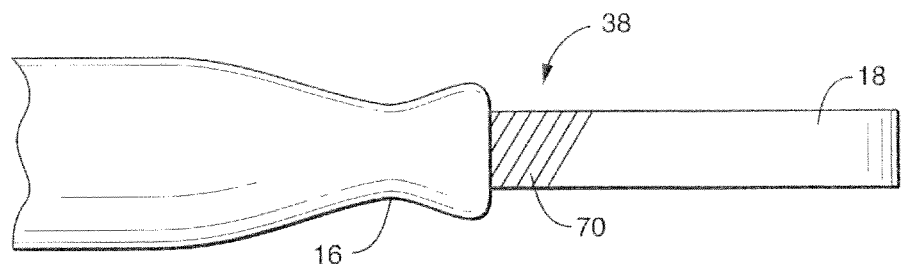
FIGS. 33-36 representatively illustrate exemplary deployment cues.

In other embodiments, the deployment cue 38 may be any suitable device for indicating that the pledget 28 has been fully deployed. For example, the deployment cue 38 may include multiple colors or patterns on the deployment element 18 wherein an indicator color or pattern only becomes visible when the pledget 28 is fully deployed. For example, as illustrated in FIG. 33, a deployment cue 38 includes a distinct pattern 70 printed on a portion of the deployment element 18 that is only visible when the deployment element 18 is fully extended and the pledget 28 is completely deployed.

Figure 34:
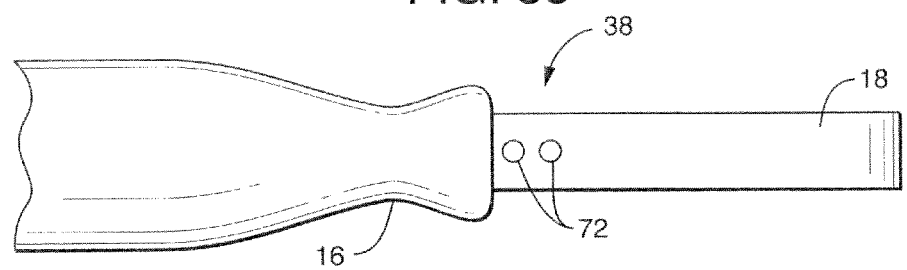

In another example, a deployment cue 38 may include a physical indicator on the deployment element 18 indicating that the pledget 28 has been fully deployed. For example, as illustrated in FIG. 34, a deployment cue 38 includes one or more raised bumps 72 positioned on a portion of the deployment element 18 that are only felt and/or seen when the deployment element 18 is fully extended and the pledget 28 is completely deployed.

Figure 35:
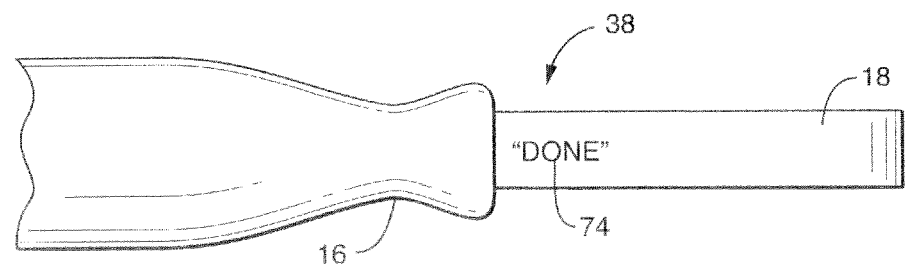

In another example, a deployment cue 38 may include a visual indicator as illustrated in FIG. 35. In FIG. 35, the deployment cue 38 includes a printed word "done" 74 positioned on a portion of the deployment element 18 that can only be read when the deployment element 18 is fully extended and the pledget 28 is completely deployed.

Figure 36:
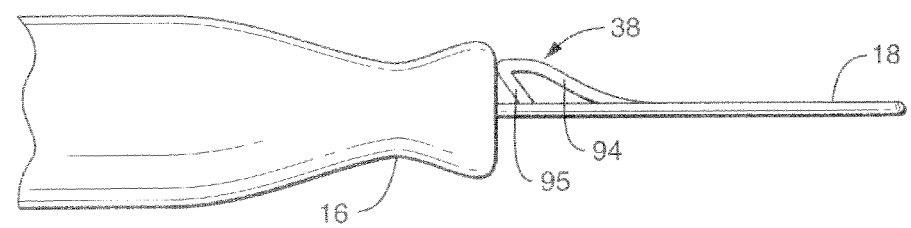

In another example, a deployment cue 38 may include a physical indicator on the deployment element 18 indicating that the pledget 28 has been fully deployed and may also provide an anti-reversing mechanism 94 as illustrated in FIG. 36. In FIG. 36, the deployment cue 38 includes an expanding element 95 joined with the deployment element 18. In various embodiments, the expanding element 95 may be made of any suitable material that can be compressed in the finger grip 16 and expands when pulled from the finger grip 16. The anti-reversing mechanism 94 is configured such that expanding element 95 cannot easily reenter the finger grip 16 after deployment.

In some embodiments, the deployment cue 38 may be a hard stop when all the reserve portion of the deployment element 18 is fully taken up and the deployment element 18 goes taut between the directional transition elements 58. This hard stop will provide a noticeable change over the normal force required to expel the pledget. In various embodiments, the force required to expel the pledget may range from about 50 grams to about 4500 grams. In other embodiments, the range may be about 100 grams to about 900 grams. The force required to expel the pledget can be measured by using any suitable universal testing machine utilizing load cells such as those manufactured by Instron®. Specifically, the pull-activated applicators may be secured between two opposing jaws wherein one jaw secures the finger grip and the other jaw secures the deployment element. The jaws start at a gauge length of 15 mm and are moved apart at a rate of 127 mm/min. The pull-activated applicator is oriented such that the pledget is expelled downward.

The deployment element 18 and the pusher 32 may be joined together in any suitable manner. In some embodiments, the pusher 32 and the deployment element 18 may be mechanically joined together. For example, as illustrated in FIGS. 6, 27, and 28, the deployment element 18 may pass through an opening 46 in the pusher 32. In some embodiments, the pusher 32 may be formed around the deployment element 18 such that the two are integrally joined. In some embodiments, the pusher 32 and the deployment element 18 may be joined by adhesive bonds, thermal bonds, ultrasonic bonds, pressure bonds, mechanical bonds, and the like, and combinations thereof. For example, the pusher 32 may be ultrasonically bonded with the deployment element 18 utilizing an energy director 130 as illustrated in FIG. 29. In other embodiments, the deployment element 18 may be tied to the pusher 32.

In some embodiments, the deployment element 18 may form a loop wherein the ends of the loop are overlapped. The loop may then be bonded to the pusher 32 at the point of overlap. In such configurations, the shear strength of the bond may be between about 250 grams and about 25,000 grams or between about 1,200 grams and about 2,400 grams. The shear strength of this bond may be determined by cutting the deployment element loop at a location opposite the overlap to create two free ends. The two free ends are clamped in opposing jaws of any suitable universal testing machine utilizing load cells and pulled apart at a 180 degree angle. The clamps start with a gauge length of 3 inches and are moved apart at a rate of 305 mm/min until the bond fails.

Figure 37:
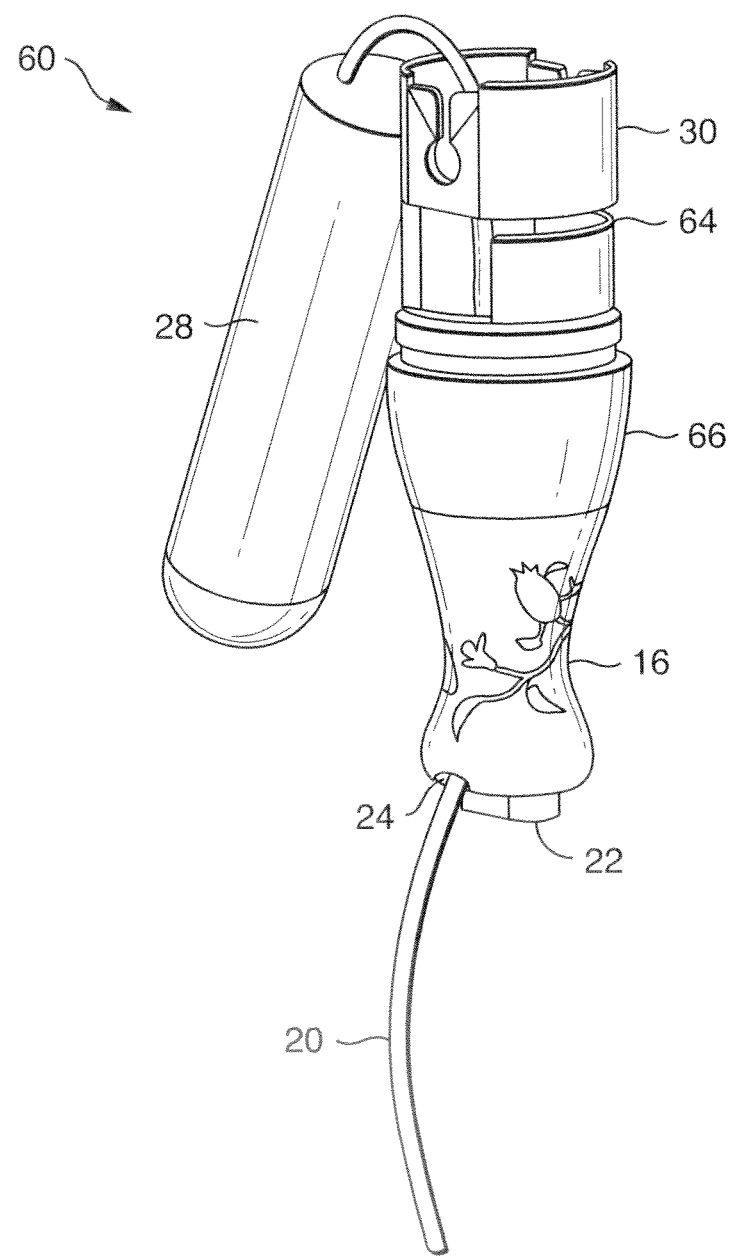
FIGS. 37-41 representatively illustrate steps in an exemplary manufacturing process to make a pull-activated applicator.
Figure 40:
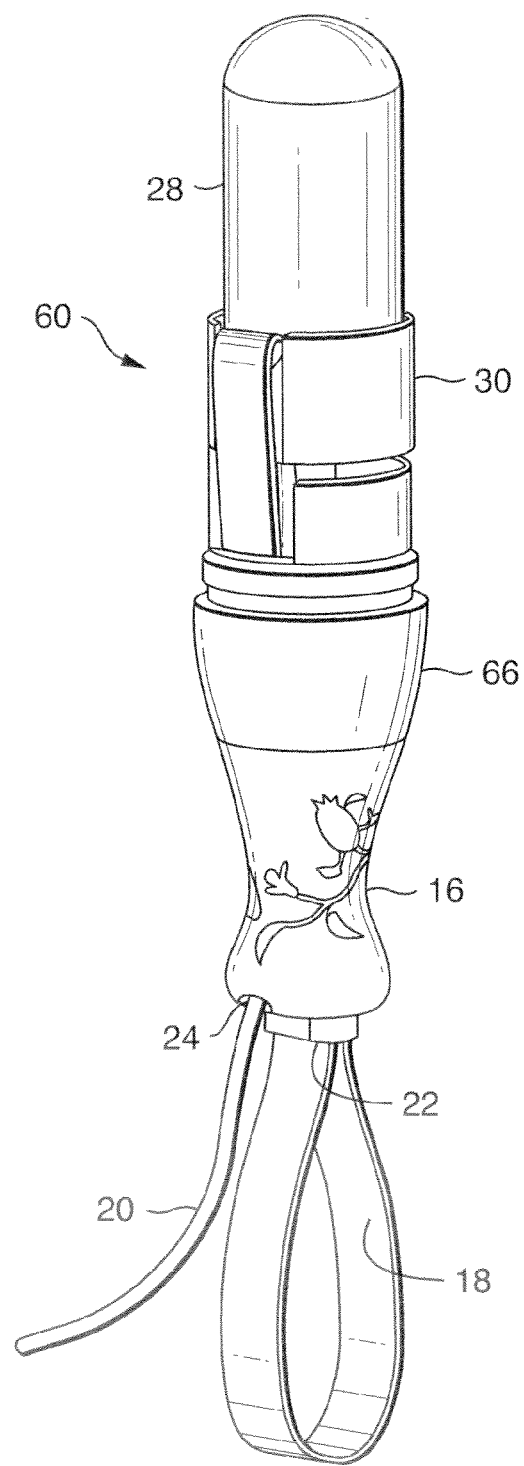
Figure 41:
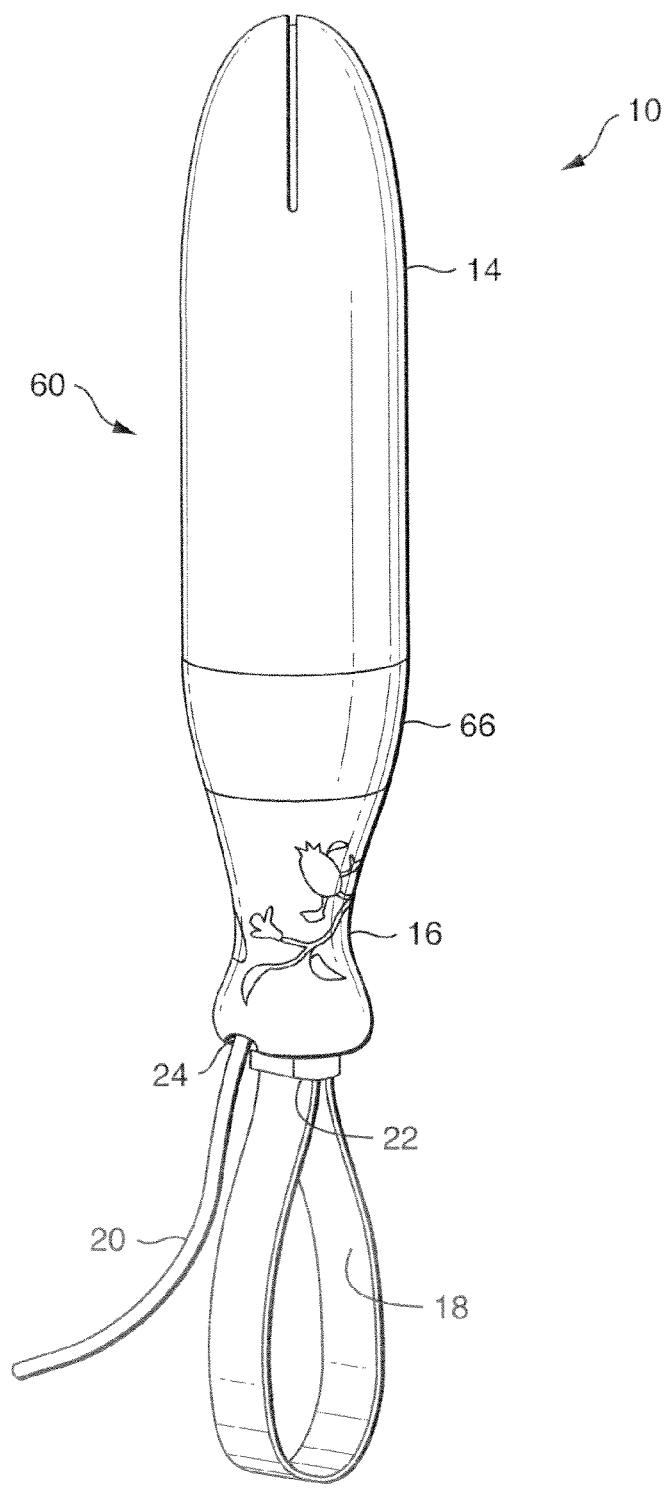

FIGS. 37-41 representatively illustrate steps in an exemplary manufacturing process 60 to make a pull-activated applicator 10. Specifically, FIG. 37 illustrates a first step in the exemplary manufacturing process 60 wherein the withdrawal string 20 is pulled through the withdrawal string opening 24 in the grip/holder assembly 66 using vacuum or any other suitable means. FIG. 38 illustrates a subsequent step in the manufacturing process 60 wherein the deployment element 18 and the pusher 32 are joined together in any suitable manner to form a deployment preassembly 62. The deployment element 18 of the deployment preassembly 62 is passed through a slit 64 in the grip/holder assembly 66. FIG. 39 illustrates a subsequent step in the manufacturing process 60 wherein the deployment element 18 of the deployment preassembly 62 is passed through the deployment element opening 22 via any suitable means such as manually, mechanically, vacuum, or the like, or combinations thereof. FIG. 40 representatively illustrates the pledget 28 being placed in the pledget holder 30 which in turn aligns the pusher in place within the grip/holder assembly 66. FIG. 41 representatively illustrates the barrel 14 being attached to the grip/holder assembly 66 via any suitable means such as a snap connection, thermal bonding, adhesive bonding, threaded connection, and the like, and combinations thereof. In some embodiments, the barrel 14 and the finger grip 16 may be formed as a single piece. Alternatively, the barrel 14 and the finger grip 16 may be formed independently and joined together mechanically, thermally, adhesively, or the like, or combinations thereof.

In some embodiments, the barrel 14 may include an internal collar and the finger grip 16 may include a seaming bead which slides over the collar to attach the two parts together. In other embodiments, the barrel 14 may include an internal seaming bead and the finger grip 16 may include a collar wherein the seaming bead slides over the collar to attach the two pieces together. In some embodiments, the barrel 14 and the finger grip 16 may be joined together in a manner that reduces or eliminates rotation between the barrel 14 and the finger grip 16. Referring now to FIG. 31, an exemplary barrel 14 is attached to an exemplary finger grip 16 using an internal collar 134 and a seaming bead 136. Specifically, the barrel 14 includes the internal collar 134 and the finger grip 16 includes the seaming bead 136. When attached, the seaming bead 136 of the finger grip 16 and the internal collar 134 move past each other to interlock.

In various embodiments, the barrel 14 and the finger grip 16 may have a joint strength of about 100 grams to about 16,000 grams or about 450 grams to about 8,000 grams. The joint strength of the barrel 14 and the finger grip 16 may be determined by securing the finger grip 16 in a first clamp such that the pull-activated applicator 10 is parallel to the ground. A platen contacts the joint between the barrel 14 and the finger grip 16 at a 90 degree angle. The platen is curved to match the contour of the barrel 14 and the finger grip 16. The platen contacts about 30% of the circumference of the pull-activated applicator 10. The platen has a thickness of about 0.5 inches as measured in the direction perpendicular to the circumferential direction of the pull-activated applicator 10. The platen moves at a rate of 127 mm/min until the barrel 14 separates from the finger grip 16. The peak load is recorded as the joint strength.

Figure 42:
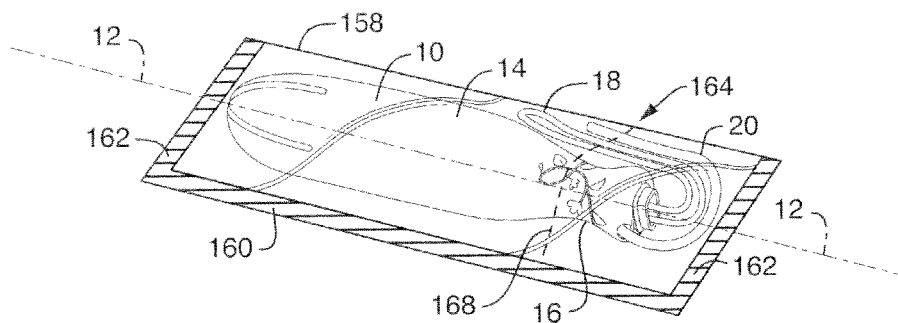
FIG. 42 is a top perspective view of an exemplary pull-activated applicator in an exemplary wrapper.
Figure 43:
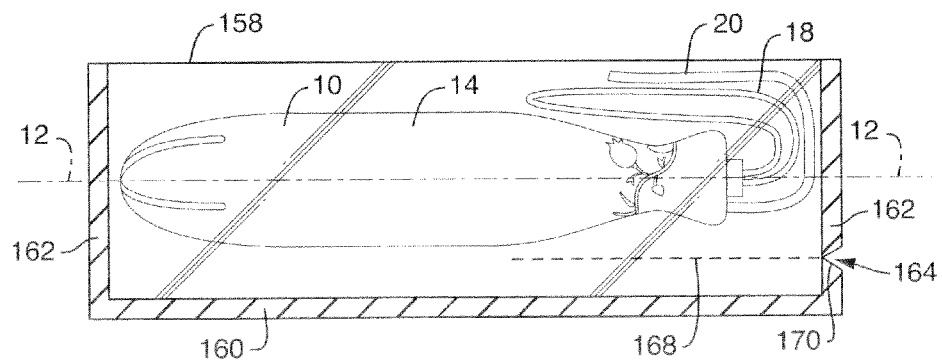
FIG. 43 is a top view of an exemplary pull-activated applicator in an exemplary wrapper.
Figure 44:
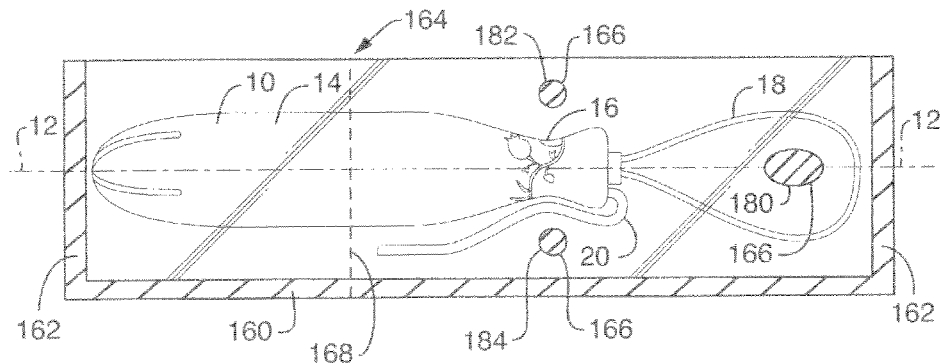
FIG. 44 is a top view of an exemplary pull-activated applicator in an exemplary wrapper.

The pull-activated applicator 10 of the present invention may be packaged in any suitable wrapper, container, carton, box, bag, tin, or the like, or combinations thereof. For example, in some embodiments, the pull-activated applicator 10 may be packaged in individual wrappers 158 as illustrated in FIGS. 42, 43, and 44. The wrappers 158 may be made of any suitable materials such as polymer films, foils, nonwoven fabrics, woven fabrics, and the like, and combinations thereof. For example, the wrappers 158 may include a paper poly foil like those commonly used in the food packaging industry. While not wishing to be bound by theory, making the wrapper 158 out of paper poly foil is believed to provide increased rigidity and strength and is believed to prevent absorption of water vapor. Additionally, paper poly foil is also believed to provide a quieter opening as well as provide a suitable surface for decorative printing.

The wrappers 158 are illustrated as being clear to better illustrate the pull-activated applicator 10 located therein. However, the wrappers 158 may have any suitable color, tint, print, or opacity. The wrappers 158 may be rolled, folded, sealed, or otherwise manipulated, or combinations thereof, to create a protective enclosure for the pull-activated applicator 10. The wrappers 158 may include any suitable opening means 164. For example, the opening means 164 may include perforations or other lines of weakness, notches for propagating tearing, flaps, pull strips, or the like, or combinations thereof. Other exemplary opening means 164 may be found in U.S. publication 2007/6156109 to Loyd. In various embodiments, the pull-activated applicator 10 of the present invention may be packaged so as to maintain control of the deployment element 18 and ensure proper presentation to the user. Other suitable wrapper configurations include those taught in U.S. Pat. No. 2,499,414 to Rabell.

Referring now to FIG. 42, a pull-activated applicator 10 is representatively illustrated in a wrapper 158. The wrapper 158 includes a side seal 160 and two end seals 162. The opening means 164 of FIG. 42 is representatively illustrated as a line of perforations 168. The perforations 168 may be located at any suitable position on the wrapper 158. For example, the perforations 168 may extend in a direction generally perpendicular to the longitudinal direction 12 as illustrated. The pull-activated applicator 10 of FIG. 42 includes a barrel 14, a finger grip 16, and a deployment element 18. In this embodiment, the deployment element 18 is folded beside the finger grip 16 to maintain control of the deployment element 18 during packaging, transportation, storage, and the like.

Referring now to FIG. 43, a top view of a pull-activated applicator 10 is representatively illustrated in a wrapper 158. The wrapper 158 includes a side seal 160 and two end seals 162. The wrapper 158 also includes an opening means 164. The opening means 164 of FIG. 43 is representatively illustrated as a notch 170 positioned at the beginning of a line of perforations 168. The perforations 168 extend in a direction generally parallel to the longitudinal direction 12.

Referring now to FIG. 44, a pull-activated applicator 10 is representatively illustrated in a wrapper 158. The wrapper 158 includes a side seal 160 and two end seals 162. The opening means 164 of FIG. 44 is representatively illustrated as a line of perforations 168. The perforations 168 may be located at any suitable position on the wrapper 158. For example, the perforations 168 may extend in a direction generally perpendicular to the longitudinal direction 12 as illustrated. The pull-activated applicator 10 of FIG. 44 includes a barrel 14, a finger grip 16, and a deployment element 18. In this embodiment, the deployment element 18 is extended beyond the finger grip 16. To maintain control of the deployment element 18 during packaging, transportation, storage, and the like, the wrapper 158 may also include any suitable number of bond points 166. For example, the wrapper 158 of FIG. 44 is illustrated with three bond points 166. The bond points 166 may be positioned at any suitable location to minimize the movement of the pull-activated applicator 10 within the wrapper 158. For example, a first bond point 180 may be positioned within a loop formed by the deployment element 18. Likewise, a second bond point 182 and a third bond point 184 may be located proximate the finger grip 16 to minimize movement of the pull-activated applicator 10 within the wrapper 158.

The pull-activated applicators of the present invention may be provided with instructions to assist a user in properly utilizing the device. The instructions may be provided on the applicator itself, on the wrapper, on the container, or combination thereof. Additionally or alternatively, the instructions may be provided as an insert that is included within the wrapper and/or the container.

In an exemplary use of the pull-activated applicator of the present invention, the finger grip may be grasped by the user with the thumb and the middle finger such that the barrel is oriented towards the body and the finger grip is oriented away from the body. The pull-activated applicator may then be inserted into the vaginal canal. Upon insertion or before insertion, the user may place their index finger through a loop provided in the deployment element. When the user is ready to expel the pledget from the applicator, they may simply extend their index finger. The extension of the user's finger pulls the deployment element in a direction away from the body and expels the pledget into the vaginal canal. This method of use provides for "one-hand" deployment.

In another exemplary use, the finger grip of the pull-activated applicator may be grasped by the user with the fingers of their hand such that the barrel is oriented towards the body and the finger grip is oriented away from the body. The pull-activated applicator may then be inserted into the vaginal canal. Upon insertion or before insertion, the user may grasp the deployment element with the fingers of their other hand. When the user is ready to expel the pledget from the applicator they may apply force to the deployment element in a direction away from the body to expel the pledget into the vaginal canal. This method of use provides for "two-hand" deployment.

The pull-activated applicators described herein may also include any suitable additive features as are known in the art. For example, the pull-activated applicators of the present invention may also include placement control features, orientation/angle features, depth control features, petal features, ergonomic features, lubrication, aesthetic features, multiple surface features, reminder features, and the like, and combinations thereof.

Exemplary depth control features are disclosed by U.S. Pat. No. 3,706,311 to Kokx and U.S. Pat. No. 4,198,978 to Nigro. Exemplary orientation features are disclosed by U.S. Pat. No. 3,706,311 to Kokx and U.S. publication 2008/0195030 to Gann. Exemplary angle features are disclosed by U.S. Pat. No. 5,788,663 to Igaue. Exemplary petal configurations are disclosed by U.S. Pat. No. 6,652,477 to Karapasha. Exemplary ergonomic features are disclosed by U.S. publication 2004/0054317 to Lemay. Exemplary lubrication features are disclosed by U.S. publication 2008/0262407 to Chase. Exemplary barrel finishes are disclosed by U.S. publication 2010/0016780 to VanDenBogart. Exemplary aesthetic features are disclosed by U.S. publication 2003/0181844 to Bernard. Exemplary reminder features are disclosed by U.S. Pat. No. 6,017,321 to Boone.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A pull-activated applicator comprising,
a barrel, a pledge, a finger grip, and a deployment element, wherein
the deployment element defines a grasping portion configured as a loop and having a starting loop size of 26 to 90 mm,
the pledget includes a withdrawal string,
the pledget is located within the barrel, and
the barrel, the pledget, and the deployment element are configured such that application of a force to the deployment element in a first direction deploys the pledget and withdrawal string from the barrel in a second direction generally opposite the first direction.

2. The pull-activated applicator of claim 1 further comprising,
a pusher, a first directional transition element, and a second directional transition element, wherein
the first directional transition element and the second directional transition element are located within the barrel,
the deployment element extends from the finger grip and is mechanically joined to the pusher such that the force applied to the deployment element in the first direction is reversed by the first directional transition element and the second directional transition element and is applied to the pusher in the second direction.

3. The pull-activated applicator of claim 1 wherein the barrel and the finger grip are formed as two separate pieces and are joined together to define an internal space.

4. The pull-activated applicator of claim 1 wherein the pledget has an elliptical cross-sectional shape and the barrel has a circular cross-sectional shape.

5. The pull-activated applicator of claim 1 wherein the deployment element has a stroke length of 40 to 50 mm.

6. The pull-activated applicator of claim 1 wherein the deployment element has an anti-reversing mechanism.

7. The pull-activated applicator of claim 1 wherein the finger grip further comprises a deployment element opening and a separate withdrawal string opening wherein,
the deployment element opening is elongated, has an elongated direction, and has the deployment element passing there through, and
the withdrawal string opening is aligned with the elongated direction and has the withdrawal string passing there through.

8. The pull-activated applicator of claim 1 wherein the finger grip further comprises a deployment element opening and a pair of flattened finger grip sides wherein,
the deployment element opening is elongated, has an elongated direction, and has the deployment element passing there through, and
the pair of flattened finger grip sides define a first plane and a second plane that are substantially parallel to each other and to the elongated direction of the deployment element opening.

* * * * *